US011529129B2

(12) United States Patent
Landey et al.

(10) Patent No.: US 11,529,129 B2
(45) Date of Patent: Dec. 20, 2022

(54) BIOPSY APPARATUS AND SYSTEM

(71) Applicant: Auris Health, Inc., Redwood City, CA (US)

(72) Inventors: Casey Teal Landey, San Francisco, CA (US); Ryan Jeffrey Connolly, San Carlos, CA (US); Jeffrey William Draper, San Francisco, CA (US); Douglas Bruce Dull, San Jose, CA (US); Don A. Tanaka, Saratoga, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 15/975,718

(22) Filed: May 9, 2018

(65) Prior Publication Data

US 2018/0325499 A1 Nov. 15, 2018

Related U.S. Application Data

(60) Provisional application No. 62/505,777, filed on May 12, 2017.

(51) Int. Cl.
*A61B 34/20* (2016.01)
*A61B 10/02* (2006.01)
(Continued)

(52) U.S. Cl.
CPC ........ *A61B 10/0233* (2013.01); *A61B 1/0016* (2013.01); *A61B 1/00149* (2013.01);
(Continued)

(58) Field of Classification Search
CPC ......... A61B 34/30; A61B 34/20; A61B 34/37; A61B 34/74; A61B 34/76; A61B 5/065;
(Continued)

(56) References Cited

U.S. PATENT DOCUMENTS 4,644,237 A 2/1987 Frushour et al.
4,745,908 A 5/1988 Wardle
(Continued)

FOREIGN PATENT DOCUMENTS

CN 1364275 8/2002
CN 1511249 7/2004
(Continued)

OTHER PUBLICATIONS

International Search Report and Written Opinion dated Aug. 2, 2018 in application No. PCT/US18/31906.
(Continued)

*Primary Examiner* — Daniel L Cerioni
(74) *Attorney, Agent, or Firm* — Chang & Hale LLP

(57) ABSTRACT

Certain aspects relate to biopsy apparatuses, systems and techniques for biopsy using a biopsy pattern. Some aspects relate to moving a distal portion of a medical instrument to one or more sample locations of the biopsy pattern and guiding the instrument to obtain tissue samples from the sample locations within the biopsy pattern. Some aspects relate to obtaining the biopsy pattern and adjusting the sample locations within the biopsy pattern based on various factors such as anatomical features.

31 Claims, 13 Drawing Sheets

(51) Int. Cl.

| | |
|---|---|
| *A61B 10/04* | (2006.01) |
| *A61B 34/30* | (2016.01) |
| *A61B 1/267* | (2006.01) |
| *A61B 1/05* | (2006.01) |
| *A61B 5/06* | (2006.01) |
| *A61B 1/06* | (2006.01) |
| *A61B 90/00* | (2016.01) |
| *A61B 1/00* | (2006.01) |
| *A61B 34/32* | (2016.01) |
| *A61B 1/07* | (2006.01) |
| *A61B 1/018* | (2006.01) |
| *A61B 5/113* | (2006.01) |
| *A61B 6/03* | (2006.01) |
| *A61B 6/12* | (2006.01) |
| *A61B 5/08* | (2006.01) |
| *A61B 90/50* | (2016.01) |
| *A61B 17/00* | (2006.01) |
| *A61B 34/10* | (2016.01) |
| *A61B 6/00* | (2006.01) |
| *A61B 90/30* | (2016.01) |
| *A61B 5/00* | (2006.01) |

(52) U.S. Cl.
CPC .............. *A61B 1/018* (2013.01); *A61B 1/05* (2013.01); *A61B 1/0684* (2013.01); *A61B 1/07* (2013.01); *A61B 1/2676* (2013.01); *A61B 5/061* (2013.01); *A61B 5/113* (2013.01); *A61B 10/04* (2013.01); *A61B 34/20* (2016.02); *A61B 34/30* (2016.02); *A61B 34/32* (2016.02); *A61B 90/37* (2016.02); *A61B 5/062* (2013.01); *A61B 5/08* (2013.01); *A61B 5/0816* (2013.01); *A61B 5/7292* (2013.01); *A61B 6/032* (2013.01); *A61B 6/12* (2013.01); *A61B 6/50* (2013.01); *A61B 90/30* (2016.02); *A61B 2010/0208* (2013.01); *A61B 2010/045* (2013.01); *A61B 2017/00207* (2013.01); *A61B 2017/00212* (2013.01); *A61B 2017/00809* (2013.01); *A61B 2034/105* (2016.02); *A61B 2034/2051* (2016.02); *A61B 2034/2063* (2016.02); *A61B 2034/2065* (2016.02); *A61B 2090/306* (2016.02); *A61B 2090/309* (2016.02); *A61B 2090/365* (2016.02); *A61B 2090/3614* (2016.02); *A61B 2090/372* (2016.02); *A61B 2090/373* (2016.02); *A61B 2090/376* (2016.02); *A61B 2090/3782* (2016.02); *A61B 2090/3966* (2016.02); *A61B 2090/502* (2016.02)

(58) Field of Classification Search
CPC . A61B 10/0233; A61B 34/32; A61B 1/00149; A61B 1/0016; A61B 1/018; A61B 1/05; A61B 1/0684; A61B 1/07; A61B 1/2676; A61B 5/061; A61B 5/113; A61B 10/04
USPC ........................................................ 600/567
See application file for complete search history.

(56) References Cited

U.S. PATENT DOCUMENTS

| | | |
|---|---|---|
| 4,748,969 A | 6/1988 | Wardle |
| 5,194,791 A | 3/1993 | Cull |
| 5,251,611 A | 10/1993 | Zehel et al. |
| 5,280,781 A | 1/1994 | Oku |
| 5,408,263 A | 4/1995 | Kikuchi |
| 5,672,877 A | 9/1997 | Liebig et al. |
| 5,769,086 A * | 6/1998 | Ritchart .............. A61B 10/0275 600/566 |
| 5,893,045 A | 4/1999 | Kusama et al. |
| 5,899,851 A | 5/1999 | Koninckx |
| 6,004,016 A | 12/1999 | Spector |
| 6,198,974 B1 | 3/2001 | Webster, Jr. |
| 6,246,200 B1 | 6/2001 | Blumenkranz et al. |
| 6,459,926 B1 | 10/2002 | Nowlin |
| 6,580,938 B1 | 6/2003 | Acker |
| 6,690,963 B2 | 2/2004 | Ben-Haim |
| 6,775,404 B1 | 8/2004 | Pagoulatos et al. |
| 6,837,846 B2 | 1/2005 | Jaffe |
| 7,197,354 B2 | 3/2007 | Sobe |
| 7,233,820 B2 | 6/2007 | Gilboa |
| 7,607,440 B2 | 10/2009 | Coste-Maniere et al. |
| 7,763,015 B2 | 7/2010 | Cooper et al. |
| 7,772,541 B2 | 8/2010 | Froggatt et al. |
| 7,901,348 B2 | 3/2011 | Soper et al. |
| 7,963,288 B2 | 6/2011 | Rosenberg et al. |
| 8,335,557 B2 | 12/2012 | Maschke |
| 8,348,931 B2 | 1/2013 | Cooper et al. |
| 8,376,934 B2 | 2/2013 | Takahashi |
| 8,396,595 B2 | 3/2013 | Dariush |
| 8,442,618 B2 | 5/2013 | Strommer et al. |
| 8,469,945 B2 | 6/2013 | Schena |
| 8,498,691 B2 | 7/2013 | Moll et al. |
| 8,506,555 B2 | 8/2013 | Ruiz Morales |
| 8,554,368 B2 | 10/2013 | Fielding et al. |
| 8,720,448 B2 | 5/2014 | Reis et al. |
| 8,738,181 B2 | 5/2014 | Greer et al. |
| 8,801,601 B2 | 8/2014 | Prisco et al. |
| 8,827,948 B2 | 9/2014 | Romo et al. |
| 8,858,424 B2 | 10/2014 | Hasegawa et al. |
| 8,894,610 B2 | 11/2014 | MacNamara et al. |
| 8,929,631 B2 | 1/2015 | Pfister et al. |
| 8,945,095 B2 | 2/2015 | Blumenkranz |
| 9,014,851 B2 | 4/2015 | Wong et al. |
| 9,023,060 B2 | 5/2015 | Cooper et al. |
| 9,129,417 B2 | 9/2015 | Zheng et al. |
| 9,173,713 B2 | 11/2015 | Hart et al. |
| 9,199,372 B2 | 12/2015 | Henderson et al. |
| 9,226,796 B2 | 1/2016 | Bowling |
| 9,256,940 B2 | 2/2016 | Carelsen et al. |
| 9,289,578 B2 | 3/2016 | Walker et al. |
| 9,302,702 B1 | 4/2016 | Schepmann |
| 9,314,306 B2 | 4/2016 | Yu |
| 9,345,456 B2 | 5/2016 | Tsonton et al. |
| 9,358,682 B2 | 6/2016 | Ruiz Morales |
| 9,452,276 B2 | 9/2016 | Duindam et al. |
| 9,504,604 B2 | 11/2016 | Alvarez |
| 9,522,034 B2 | 12/2016 | Johnson |
| 9,561,083 B2 | 2/2017 | Yu et al. |
| 9,622,827 B2 | 4/2017 | Yu et al. |
| 9,629,595 B2 | 4/2017 | Walker et al. |
| 9,636,184 B2 | 5/2017 | Lee et al. |
| 9,675,422 B2 | 6/2017 | Hourtash et al. |
| 9,713,509 B2 | 7/2017 | Schuh et al. |
| 9,717,563 B2 | 8/2017 | Tognaccini |
| 9,726,476 B2 | 8/2017 | Ramamurthy et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,789,608 B2 | 10/2017 | Itkowitz et al. |
| 9,818,681 B2 | 11/2017 | Machida |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 10,016,900 B1 | 7/2018 | Meyer et al. |
| 10,022,192 B1 | 7/2018 | Ummalaneni |
| 10,145,747 B1 | 12/2018 | Lin et al. |
| 10,159,532 B1 | 12/2018 | Ummalaneni et al. |
| 10,213,264 B2 | 2/2019 | Tanner et al. |
| 10,434,660 B2 | 10/2019 | Meyer |

(56) References Cited

U.S. PATENT DOCUMENTS

| | | |
|---|---|---|
| 10,454,347 B2 | 10/2019 | Covington et al. |
| 10,464,209 B2 | 11/2019 | Ho et al. |
| 10,470,830 B2 | 11/2019 | Hill |
| 10,482,599 B2 | 11/2019 | Mintz et al. |
| 10,517,692 B2 | 12/2019 | Eyre et al. |
| 10,524,866 B2 | 1/2020 | Srinivasan |
| 10,539,478 B2 | 1/2020 | Lin |
| 10,639,114 B2 | 5/2020 | Schuh |
| 2001/0000040 A1 | 3/2001 | Adams et al. |
| 2001/0021843 A1 | 9/2001 | Bosselmann et al. |
| 2002/0035330 A1 | 3/2002 | Cline |
| 2002/0062062 A1 | 5/2002 | Belson et al. |
| 2002/0077533 A1 | 6/2002 | Bieger et al. |
| 2002/0161280 A1 | 10/2002 | Chatenever et al. |
| 2002/0173878 A1 | 11/2002 | Watanabe |
| 2003/0045778 A1 | 3/2003 | Ohline |
| 2003/0181809 A1 | 9/2003 | Hall et al. |
| 2003/0182091 A1 | 9/2003 | Kukuk |
| 2004/0072066 A1 | 4/2004 | Cho et al. |
| 2004/0257021 A1 | 12/2004 | Chang et al. |
| 2005/0043718 A1 | 2/2005 | Madhani |
| 2005/0065400 A1 | 3/2005 | Banik |
| 2005/0107917 A1 | 5/2005 | Smith et al. |
| 2005/0222554 A1 | 10/2005 | Wallace et al. |
| 2005/0234293 A1 | 10/2005 | Yamamoto |
| 2005/0256398 A1 | 11/2005 | Hastings |
| 2005/0261551 A1 | 11/2005 | Couvillon |
| 2005/0267359 A1 | 12/2005 | Hussaini et al. |
| 2005/0272975 A1 | 12/2005 | McWeeney et al. |
| 2006/0015096 A1 | 1/2006 | Hauck et al. |
| 2006/0041293 A1 | 2/2006 | Mehdizadeh |
| 2006/0079745 A1 | 4/2006 | Viswanathan et al. |
| 2006/0189891 A1 | 8/2006 | Waxman et al. |
| 2006/0200026 A1 | 9/2006 | Wallace et al. |
| 2006/0200049 A1 | 9/2006 | Leo et al. |
| 2006/0258938 A1 | 11/2006 | Hoffman et al. |
| 2007/0013336 A1 | 1/2007 | Nowlin et al. |
| 2007/0043455 A1 | 2/2007 | Viswanathan |
| 2007/0106147 A1 | 5/2007 | Altmann et al. |
| 2007/0135886 A1 | 6/2007 | Maschke |
| 2007/0142971 A1 | 6/2007 | Schena |
| 2007/0150155 A1 | 6/2007 | Kawai |
| 2007/0156019 A1 | 7/2007 | Larkin et al. |
| 2007/0249911 A1 | 10/2007 | Simon |
| 2007/0253599 A1 | 11/2007 | White et al. |
| 2007/0287992 A1 | 12/2007 | Diolaiti |
| 2007/0293721 A1 | 12/2007 | Gilboa |
| 2007/0299353 A1 | 12/2007 | Harlev et al. |
| 2008/0027313 A1 | 1/2008 | Shachar |
| 2008/0046122 A1 | 2/2008 | Manzo et al. |
| 2008/0108870 A1 | 5/2008 | Wiita et al. |
| 2008/0123921 A1 | 5/2008 | Gielen et al. |
| 2008/0140087 A1 | 6/2008 | Barbagli et al. |
| 2008/0147089 A1 | 6/2008 | Loh |
| 2008/0159653 A1 | 7/2008 | Dunki-Jacobs et al. |
| 2008/0231221 A1 | 9/2008 | Ogawa |
| 2008/0249640 A1 | 10/2008 | Vittor et al. |
| 2008/0255505 A1 | 10/2008 | Carlson et al. |
| 2008/0312771 A1 | 12/2008 | Sugiura |
| 2009/0005768 A1 | 1/2009 | Sharareh |
| 2009/0062813 A1 | 3/2009 | Prisco |
| 2009/0076534 A1 | 3/2009 | Shelton |
| 2009/0184825 A1 | 7/2009 | Anderson |
| 2009/0198298 A1 | 8/2009 | Kaiser et al. |
| 2009/0227861 A1 | 9/2009 | Ganatra et al. |
| 2009/0245600 A1 | 10/2009 | Hoffman |
| 2009/0256905 A1 | 10/2009 | Tashiro |
| 2009/0287354 A1 | 11/2009 | Choi |
| 2009/0324161 A1 | 12/2009 | Prisco |
| 2010/0030061 A1 | 2/2010 | Canfield |
| 2010/0030115 A1 | 2/2010 | Fujimoto |
| 2010/0069920 A1 | 3/2010 | Naylor et al. |
| 2010/0076263 A1 | 3/2010 | Tanaka |
| 2010/0121138 A1 | 5/2010 | Goldenberg et al. |
| 2010/0168918 A1 | 7/2010 | Zhao |
| 2010/0204713 A1 | 8/2010 | Ruiz |
| 2010/0228266 A1 | 9/2010 | Hourtash |
| 2010/0234856 A1 | 9/2010 | Stoianovici et al. |
| 2010/0256812 A1 | 10/2010 | Tsusaka et al. |
| 2011/0009880 A1 | 1/2011 | Prisco |
| 2011/0021926 A1 | 1/2011 | Spencer |
| 2011/0082366 A1 | 4/2011 | Scully et al. |
| 2011/0082462 A1 | 4/2011 | Suarez |
| 2011/0137122 A1 | 6/2011 | Kawai |
| 2011/0153252 A1 | 6/2011 | Govari |
| 2011/0160570 A1 | 6/2011 | Kariv |
| 2011/0196199 A1 | 8/2011 | Donhowe et al. |
| 2011/0218676 A1 | 9/2011 | Okazaki |
| 2011/0257480 A1 | 10/2011 | Takahashi |
| 2011/0258842 A1 | 10/2011 | Dukesherer et al. |
| 2011/0319910 A1 | 12/2011 | Roelle et al. |
| 2012/0000427 A1 | 1/2012 | Nilsson |
| 2012/0035440 A1 | 2/2012 | Ferren et al. |
| 2012/0046522 A1 | 2/2012 | Naito |
| 2012/0059249 A1 | 3/2012 | Verard et al. |
| 2012/0069167 A1 | 3/2012 | Liu et al. |
| 2012/0071752 A1 | 3/2012 | Sewell |
| 2012/0071822 A1 | 3/2012 | Romo et al. |
| 2012/0071894 A1 | 3/2012 | Tanner et al. |
| 2012/0123441 A1 | 5/2012 | Au |
| 2012/0130217 A1 | 5/2012 | Kauphusman et al. |
| 2012/0209293 A1 | 8/2012 | Carlson |
| 2012/0215094 A1 | 8/2012 | Rahimian et al. |
| 2012/0253276 A1 | 10/2012 | Govari et al. |
| 2012/0283745 A1 | 11/2012 | Goldberg et al. |
| 2012/0289777 A1 | 11/2012 | Chopra |
| 2012/0302869 A1 | 11/2012 | Koyrakh |
| 2012/0328077 A1 | 12/2012 | Bouvier |
| 2013/0018306 A1 | 1/2013 | Ludwin |
| 2013/0085330 A1 | 4/2013 | Ramamurthy et al. |
| 2013/0090530 A1 | 4/2013 | Ramamurthy |
| 2013/0102846 A1 | 4/2013 | Sjostrom |
| 2013/0131503 A1 | 5/2013 | Schneider et al. |
| 2013/0144116 A1 | 6/2013 | Cooper et al. |
| 2013/0165854 A1 | 6/2013 | Sandhu et al. |
| 2013/0165945 A9 | 6/2013 | Roelle |
| 2013/0204124 A1 | 8/2013 | Duindam |
| 2013/0218005 A1 | 8/2013 | Desai |
| 2013/0303891 A1 | 11/2013 | Chopra |
| 2013/0303892 A1 | 11/2013 | Zhao |
| 2013/0305138 A1* | 11/2013 | Gicovate ............... G06F 40/143 715/234 |
| 2013/0325030 A1 | 12/2013 | Hourtash et al. |
| 2014/0058428 A1 | 2/2014 | Christopher et al. |
| 2014/0114180 A1 | 4/2014 | Jain |
| 2014/0135985 A1 | 5/2014 | Coste-Maniere et al. |
| 2014/0142591 A1 | 5/2014 | Alvarez et al. |
| 2014/0163664 A1 | 6/2014 | Goldsmith |
| 2014/0222207 A1 | 8/2014 | Bowling et al. |
| 2014/0235943 A1 | 8/2014 | Paris |
| 2014/0277333 A1 | 9/2014 | Lewis et al. |
| 2014/0296870 A1 | 10/2014 | Stern et al. |
| 2014/0309649 A1 | 10/2014 | Alvarez et al. |
| 2014/0316420 A1 | 10/2014 | Ballard et al. |
| 2014/0343416 A1 | 11/2014 | Panescu |
| 2014/0343569 A1 | 11/2014 | Turner |
| 2014/0357984 A1 | 12/2014 | Wallace et al. |
| 2014/0364870 A1 | 12/2014 | Alvarez et al. |
| 2014/0379000 A1 | 12/2014 | Romo et al. |
| 2015/0051592 A1 | 2/2015 | Kintz |
| 2015/0073267 A1 | 3/2015 | Brannan |
| 2015/0088161 A1 | 3/2015 | Hata |
| 2015/0101442 A1 | 4/2015 | Romo |
| 2015/0104284 A1 | 4/2015 | Riedel |
| 2015/0119628 A1 | 4/2015 | Bharat et al. |
| 2015/0119638 A1 | 4/2015 | Yu et al. |
| 2015/0150635 A1 | 6/2015 | Kilroy |
| 2015/0164594 A1 | 6/2015 | Romo et al. |
| 2015/0164596 A1 | 6/2015 | Romo |
| 2015/0202015 A1 | 7/2015 | Elhawary |
| 2015/0223902 A1 | 8/2015 | Walker et al. |
| 2015/0255782 A1 | 9/2015 | Kim et al. |
| 2015/0265359 A1 | 9/2015 | Camarillo |
| 2015/0265807 A1 | 9/2015 | Park et al. |

(56) References Cited

U.S. PATENT DOCUMENTS

| | | |
|---|---|---|
| 2015/0297864 A1 | 10/2015 | Kokish et al. |
| 2015/0305650 A1 | 10/2015 | Hunter |
| 2015/0311838 A1 | 10/2015 | Moule |
| 2015/0313503 A1 | 11/2015 | Seibel et al. |
| 2015/0335480 A1 | 11/2015 | Alvarez et al. |
| 2015/0342695 A1 | 12/2015 | He |
| 2015/0359597 A1 | 12/2015 | Gombert et al. |
| 2015/0374956 A1 | 12/2015 | Bogusky |
| 2016/0000414 A1 | 1/2016 | Brown et al. |
| 2016/0000495 A1 | 1/2016 | Elliott |
| 2016/0001038 A1 | 1/2016 | Romo et al. |
| 2016/0005168 A1 | 1/2016 | Merlet |
| 2016/0005220 A1 | 1/2016 | Weingarten |
| 2016/0005576 A1 | 1/2016 | Tsukamoto |
| 2016/0016319 A1 | 1/2016 | Remirez |
| 2016/0045269 A1 | 2/2016 | Elhawary et al. |
| 2016/0051221 A1 | 2/2016 | Dickhans et al. |
| 2016/0066794 A1 | 3/2016 | Klinder et al. |
| 2016/0073928 A1* | 3/2016 | Soper .................. A61B 1/0008 600/424 |
| 2016/0075030 A1 | 3/2016 | Takahashi |
| 2016/0081568 A1 | 3/2016 | Kolberg |
| 2016/0100772 A1 | 4/2016 | Ikuma |
| 2016/0120521 A1 | 5/2016 | Weingarten et al. |
| 2016/0128992 A1 | 5/2016 | Hudson |
| 2016/0183841 A1 | 6/2016 | Duindam et al. |
| 2016/0206389 A1 | 7/2016 | Miller |
| 2016/0228032 A1 | 8/2016 | Walker et al. |
| 2016/0270865 A1 | 9/2016 | Landey et al. |
| 2016/0278865 A1 | 9/2016 | Capote |
| 2016/0287053 A1 | 10/2016 | Miura |
| 2016/0287111 A1 | 10/2016 | Jacobsen |
| 2016/0287279 A1 | 10/2016 | Bovay et al. |
| 2016/0287346 A1 | 10/2016 | Hyodo et al. |
| 2016/0296294 A1 | 10/2016 | Moll et al. |
| 2016/0331469 A1 | 11/2016 | Hall et al. |
| 2016/0338787 A1 | 11/2016 | Popovic |
| 2016/0346038 A1 | 12/2016 | Helgeson |
| 2016/0346924 A1 | 12/2016 | Hasegawa |
| 2016/0354057 A1 | 12/2016 | Hansen et al. |
| 2016/0360947 A1 | 12/2016 | Iida |
| 2016/0360949 A1 | 12/2016 | Hyodo |
| 2016/0372743 A1 | 12/2016 | Cho et al. |
| 2016/0374541 A1 | 12/2016 | Agrawal et al. |
| 2017/0007337 A1 | 1/2017 | Dan |
| 2017/0056215 A1 | 3/2017 | Nagesh et al. |
| 2017/0065364 A1 | 3/2017 | Schuh et al. |
| 2017/0065365 A1 | 3/2017 | Schuh |
| 2017/0068796 A1 | 3/2017 | Passerini et al. |
| 2017/0100197 A1 | 4/2017 | Zubiate |
| 2017/0100199 A1 | 4/2017 | Yu et al. |
| 2017/0106904 A1 | 4/2017 | Hanson |
| 2017/0119413 A1 | 5/2017 | Romo |
| 2017/0119481 A1 | 5/2017 | Romo et al. |
| 2017/0151027 A1 | 6/2017 | Walker et al. |
| 2017/0165011 A1 | 6/2017 | Bovay et al. |
| 2017/0165503 A1 | 6/2017 | Hautvast et al. |
| 2017/0172673 A1 | 6/2017 | Yu et al. |
| 2017/0189118 A1 | 7/2017 | Chopra |
| 2017/0202627 A1 | 7/2017 | Sramek et al. |
| 2017/0209073 A1 | 7/2017 | Sramek et al. |
| 2017/0245854 A1 | 8/2017 | Zemlok |
| 2017/0245885 A1* | 8/2017 | Lenker ............... A61B 17/3478 |
| 2017/0251988 A1 | 9/2017 | Weber et al. |
| 2017/0280978 A1 | 10/2017 | Yamamoto |
| 2017/0281049 A1 | 10/2017 | Yamamoto |
| 2017/0290631 A1 | 10/2017 | Lee et al. |
| 2017/0303889 A1* | 10/2017 | Grim .................. A61B 8/462 |
| 2017/0304015 A1 | 10/2017 | Tavallaei et al. |
| 2017/0325715 A1 | 11/2017 | Mehendale et al. |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0064498 A1 | 3/2018 | Kapadia |
| 2018/0177383 A1 | 6/2018 | Noonan et al. |
| 2018/0177556 A1 | 6/2018 | Noonan et al. |
| 2018/0177561 A1 | 6/2018 | Mintz et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0250085 A1 | 9/2018 | Simi |
| 2018/0271604 A1 | 9/2018 | Grout et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0083183 A1 | 3/2019 | Moll et al. |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0167366 A1 | 6/2019 | Ummalaneni |
| 2019/0167367 A1 | 6/2019 | Walker et al. |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0209252 A1 | 7/2019 | Walker et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0008874 A1* | 1/2020 | Barbagli ............... A61M 25/01 |
| 2020/0022767 A1 | 1/2020 | Hill |
| 2020/0038123 A1 | 2/2020 | Graetzel |
| 2020/0039086 A1 | 2/2020 | Meyer |
| 2020/0046434 A1 | 2/2020 | Graetzel |
| 2020/0054408 A1 | 2/2020 | Schuh et al. |
| 2020/0060516 A1 | 2/2020 | Baez |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |

(56) References Cited

U.S. PATENT DOCUMENTS

| | | |
|---|---|---|
| 2020/0237458 A1 | 7/2020 | DeFonzo |
| 2020/0246591 A1 | 8/2020 | Bogusky |
| 2020/0261172 A1 | 8/2020 | Romo |
| 2020/0268459 A1 | 8/2020 | Noonan et al. |
| 2020/0268460 A1 | 8/2020 | Tse |

FOREIGN PATENT DOCUMENTS

| | | |
|---|---|---|
| CN | 1846181 | 10/2006 |
| CN | 1857877 | 11/2006 |
| CN | 101325920 | 12/2008 |
| CN | 102316817 | 1/2012 |
| CN | 102458295 | 5/2012 |
| CN | 102711586 | 10/2012 |
| CN | 102973317 | 3/2013 |
| CN | 103565529 | 2/2014 |
| CN | 103735313 | 4/2014 |
| CN | 103767659 | 5/2014 |
| CN | 103930063 | 7/2014 |
| CN | 104271075 A | 1/2015 |
| CN | 104684502 | 6/2015 |
| CN | 105030331 | 11/2015 |
| CN | 105559850 | 5/2016 |
| CN | 105559886 | 5/2016 |
| CN | 105611881 | 5/2016 |
| CN | 107028659 | 8/2017 |
| CN | 104931059 | 9/2018 |
| DE | 19845267 C1 | 5/2000 |
| DE | 102013100605 | 7/2014 |
| EP | 1 250 986 | 10/2002 |
| EP | 1 566 150 | 8/2005 |
| EP | 1 800 593 | 6/2007 |
| EP | 2 158 834 | 3/2010 |
| EP | 2 392 435 | 12/2011 |
| EP | 3 025 630 | 6/2016 |
| JP | 2005334650 A | 12/2005 |
| JP | 2008-528130 | 7/2008 |
| JP | 2009-509654 | 3/2009 |
| JP | 2009-524530 | 7/2009 |
| JP | 2011-088260 | 5/2011 |
| JP | 2013-510662 | 3/2013 |
| RU | 2569699 C2 | 11/2015 |
| WO | 1991009375 A1 | 6/1991 |
| WO | WO 01/56457 | 8/2001 |
| WO | 03028547 A2 | 4/2003 |
| WO | WO 04/029782 | 4/2004 |
| WO | WO 05/087128 | 9/2005 |
| WO | WO 06/122061 | 11/2006 |
| WO | WO 09/120940 | 10/2009 |
| WO | 2008065600 A3 | 11/2009 |
| WO | 2009148317 A1 | 12/2009 |
| WO | 2008111070 A3 | 2/2010 |
| WO | WO 11/132409 | 10/2011 |
| WO | WO 12/044334 | 4/2012 |
| WO | WO 14/114551 | 7/2014 |
| WO | 2015061756 A1 | 4/2015 |
| WO | WO 15/142957 | 9/2015 |
| WO | 2016032848 A1 | 3/2016 |
| WO | WO 17/048194 | 3/2017 |

OTHER PUBLICATIONS

Verdaasdonk et al., Jan. 23, 2013, Effect of microsecond pulse length and tip shape on explosive bubble formation of 2.78 µm Er,Cr;YSGG and 2.94 µm Er:YAG laser, Proceedings of SPIE, vol. 8221, 12.

Blankenstein, Jun. 2008, Dynamic Registration and High Speed Visual Servoing in Robot-Assisted Surgery, Katholieke Universiteit Leuven, Leuven, Belgium.

Lawton et al., 1999, Ribbons and groups: A thin rod theory for catheters and filaments, J. Phys. A., 1999, 32:1709-1735.

EP search report for appl No. 18799192.2, dated Jan. 19, 2021, 6 pages.

Devin V. Amin et al., Ultrasound Registration of the Bone Surface for Surgical Navigation, Computer Aided Surgery, 8:1-16, 2003, 17 pages.

Heinz-Theo Luebbers et al., Comparison of different registration methods for surgical navigation in cranio-maxillofacial surgery, Journal of Cranio-Maxillofacial Surgery, 36:109-116, 2008, 8 pages.

Intuitive, System, Instruments, and Accessories User Manual, 91 pages.

Ion by Intuitive, available at https://www.intuitive.com/en-us/products-and-services/ion, last accessed Aug. 12, 2021, 6 pages.

Jeffrey H. Shuhaiber, Augmented Reality in Surgery, Archive of Surgery, 139:170-174, Feb. 2004, 5 pages.

Matthias Baumhauer et al., Navigation in Endoscopic Soft Tissue Surgery—Perspectives and Limitations, Journal of Endourology, 22(4):1-15, 2008, 16 pages.

microBIRD Product Brochure, Ascension Technology Corporation, available at http://www.ascension-tech.com/products/microbird.php, Jun. 12, 2019, 3 pages.

Robert Galloway & Terry Peters, Chapter 1: Overview and History of Image-Guided Interventions; David Holmes III et al, Chapter 3: Visualization in Image-Guided Interventions; Ziv Yaniv, Chapter 6: Rigid Registration, in Image-Guided Interventions: Technology and Applications, Terry Peters & Kevin Cleary eds., 2008, 95 pages.

Sargent, Dusty & Chen, Chao-I & Wang, Yuanfang, Cross Modality Registration of Video and Magnetic Tracker Data for 3D Appearance and Structure Modeling. Proceedings of SPIE—The International Society for Optical Engineering, 2010, 8 pages.

Notice of Grant for CN Appl. No. 19106292P, dated May 24, 2022, 1 page.

Office Action for Appl. No. 2019562319, dated Apr. 26, 2022, 5 pages.

Kukuk, Oct. 5, 2001, TBNA-protocols: Guiding TransBronchial Needle Aspirations Without a Computer in the Operating Room, MICCAI 2001, 2208:997-1006.

Verdaasdonk et al., Jan. 23, 2013, Effect of microsecond pulse length and tip shape on explosive bubble formation of 2.78 µ Er,Cr;YSGG and 2.94 µ Er:YAG laser, Proceedings of SPIE, vol. 8221, 12.

CN Office Action and Search Report for appl No. 201880038750.4, dated Nov. 16, 2021, 10 pages.

* cited by examiner

BIOPSY APPARATUS AND SYSTEM

CROSS-REFERENCE TO RELATED APPLICATION

This application claims the benefit of U.S. Provisional Application No. 62/505,777, filed May 12, 2017, which is hereby incorporated by reference in its entirety.

TECHNICAL FIELD

The systems and methods disclosed herein are directed to medical procedures, and, more particularly, to a biopsy system and apparatus.

BACKGROUND

Many procedures require navigation within an anatomy of a patient and some interaction with a tissue site. For example, bronchoscopy is a medical procedure that allows a physician to examine the inside conditions of a patient's lung airways, such as bronchi and bronchioles. During the medical procedure, a thin, flexible tubular tool, known as a bronchoscope, may be inserted into the patient's mouth and passed down the patient's throat into his/her lung airways towards a target tissue site identified for subsequent diagnosis and treatment. The bronchoscope can have an interior lumen (a "working channel") providing a pathway to the target tissue site, and catheters and various medical tools can be inserted through the working channel to the target tissue site. In some circumstances, a tool can be inserted through the working channel to take a biopsy from the target tissue site.

SUMMARY

The systems, methods and devices of this disclosure each have several innovative aspects, no single one of which is solely responsible for the desirable attributes disclosed herein.

One aspect relates to a system configured to aid obtaining a set of one or more biopsy samples from a tissue site, the system comprising an instrument through which the one or more biopsy samples can be collected; an actuator configured to control movements of the instrument; at least one computer-readable memory having stored thereon executable instructions; and one or more processors in communication with the at least one computer-readable memory and configured to execute the instructions to cause the system to at least: access a biopsy pattern comprising one or more sample locations within the tissue site; calculate movement of the instrument according to the biopsy pattern; and move the instrument to one or more positions corresponding to the one or more sample locations.

Some implementations may further comprise a user input device configured to receive information from a user. Some implementations may further comprise a user interface screen configured to show the biopsy pattern.

In some implementations, the one or more processors are configured to execute the instructions to cause the system to at least: adjust the biopsy pattern or a route representing the movement of the instrument to the one or more positions based on information from the user.

Some implementations may further comprise a set of one or more location sensors; and wherein the one or more processors are configured to execute the instructions to cause the system to at least: calculate (1) at least one position of the set of location sensors or (2) a position of a distal end of the instrument based on a data signal from the set of location sensors; and control movement to the one or more positions based on the calculated position.

In some implementations, at least one of the set of location sensors comprises a camera at a distal end of the instrument. In some implementations, at least one of the set of location sensors comprises an ultrasound transducer at a distal end of the instrument. In some implementations, the ultrasound transducer comprises a radial-scanning or linear-scanning transducer. In some implementations, at least one of the set of location sensors comprises an electromagnetic (EM) sensor at a distal end of the instrument. In some implementations, at least one of the set of location sensors comprises an X-ray image intensifier and an X-ray imaging device.

In some implementations, the instrument comprises a scope configured to reach the tissue site; wherein the actuator is configured to control movements of the scope; and wherein the one or more processors are configured to execute the instructions to cause the system to at least: calculate movement of the scope according to the biopsy pattern; and cause the actuator to move the scope to one or more positions corresponding to the one or more sample locations.

In some implementations, the instrument comprises: a scope configured to reach the tissue site; and a collection device configured to (1) removably place within the scope or (2) pass through the scope and collect the one or more biopsy samples. In some implementations, the scope is an endoscope. In some implementations, the one or more processors are further configured to execute the instructions to cause the system to at least: position the scope to a first position, confirm receiving a first sample, and position the scope to a second position in response to a confirmation of receiving the first sample.

In some implementations, the instrument comprises a collection device configured to obtain the one or more biopsy samples; wherein the actuator is configured to control movements of the collection device; and wherein the one or more processors are configured to execute the instructions to cause the system to at least: calculate movement of the collection device according to the biopsy pattern; and move the collection device to one or more positions corresponding to the one or more sample locations.

In some implementations, the one or more processors are further configured to execute the instructions to cause the system to at least: actuate the collection device to obtain the one or more biopsy samples from the one or more positions corresponding to the one or more sample locations. In some implementations, the collection device comprises a needle. In some implementations, the collection device further comprises a marker at a distal end of the collection device; and wherein the one or more processors are further configured to execute the instructions to cause the system to at least: determine movement of the collection device according to a movement of the marker; and adjust the one or more sample locations according to the movement of the collection device.

In some implementations, the biopsy pattern comprises one or more sample positions arranged in at least two dimensions. In some implementations, the biopsy pattern comprises one or more sample positions arranged in a shape fitted to a shape of the tissue site. In some implementations, the biopsy pattern comprises one or more sample positions arranged in a shape whose center is within the tissue site. In some implementations, the biopsy pattern comprises one or more sample positions at least one of which corresponds to a center of the tissue site. In some implementations, the biopsy pattern comprises one or more sample positions arranged in a circle or a grid. In some implementations, the biopsy pattern further comprises one or more penetration depths, one or more sampling velocities, one or more sampling intervals, or one or more sampling forces corresponding to the one or more sample positions.

Another aspect relates to an apparatus configured to aid obtaining one or more biopsy samples from a tissue site, the apparatus comprising: at least one computer-readable memory having stored thereon executable instructions; and one or more processors in communication with the at least one computer-readable memory and configured to execute the instructions to cause the apparatus to at least: determine a pattern for taking one or more biopsy samples from the tissue site, the pattern comprising one or more sample positions arranged in at least two dimensions; determine a procedure plan for movement of a distal portion of an instrument of a robotic medical system based on the pattern; and guide the distal portion of the instrument to one or more locations corresponding to the at least two dimensional pattern.

In some implementations, one or more processors in communication with the at least one computer-readable memory and configured to execute the instructions to cause the apparatus to at least: save the procedure plan to the at least one computer-readable memory. In some implementations, one or more processors in communication with the at least one computer-readable memory and configured to execute the instructions to cause the apparatus to at least: transfer the procedure plan to the robotic medical system to guide the distal portion of the instrument of the robotic medical system. In some implementations, the one or more processors are configured to execute the instructions to cause the apparatus to at least: calculate (1) at least one position of a set of location sensors or (2) a position of the distal portion of the instrument based on a data signal from the set of location sensors; and control movement of the instrument based on the calculated position.

In some implementations, at least one of the set of location sensors comprises an ultrasound transducer at the distal portion of the instrument. In some implementations, the ultrasound transducer comprises a radial-scanning or linear-scanning transducer. In some implementations, at least one of the set of location sensors comprises an EM sensor at the distal portion of the instrument. In some implementations, at least one of the set of location sensors comprises an X-ray image intensifier and an X-ray imaging device.

In some implementations, the one or more processors are configured to execute the instructions to cause the apparatus to at least: calculate movement of a scope according to the pattern; and guide a distal portion of the scope to the one or more locations corresponding to the pattern.

In some implementations, the one or more processors are configured to execute the instructions to cause the apparatus to at least: calculate movement of a collection device according to the pattern; and guide a distal portion of the collection device to the one or more locations corresponding to the pattern.

In some implementations, the one or more processors are configured to execute the instructions to cause the apparatus to at least: actuate the collection device to obtain the one or more biopsy samples from the one or more locations corresponding to the pattern. In some implementations, the one or more processors are configured to execute the instructions to cause the apparatus to at least: in response to the collection device's collection of the biopsy samples, calculate one or more sampling locations at which the collection device obtains the biopsy samples based on the movement of the marker; compare between the one or more sampling locations and the one or more sample locations of the biopsy pattern; and adjust the one or more sample locations of the biopsy pattern based on the one or more sampling locations.

In some implementations, the pattern comprises one or more sample positions arranged in a shape fitted to a shape of the tissue site. In some implementations, the pattern comprises one or more sample positions arranged in a shape whose center is within the tissue site. In some implementations, the pattern comprises one or more sample positions at least one of which corresponds to a center of the tissue site. In some implementations, the pattern comprises one or more sample positions arranged in a circle or a grid. In some implementations, the pattern further comprises one or more penetration depths, one or more sampling velocities, one or more sampling intervals, or one or more sampling forces corresponding to the one or more sample positions.

Yet another aspect relates to a method for collecting one or more samples from a target tissue site of a patient, the method comprising: through a user interface of a robotic medical system, receiving an user input that selects a pattern for the one or more samples within the target tissue site; moving a distal portion of an instrument of the robotic medical system to a first position corresponding to a first sample location within the pattern; guiding the instrument to obtain a first tissue sample at the first sample location within the pattern; moving the distal portion of the instrument of the robotic medical system to a second position corresponding to a second sample location within the pattern; and guiding the instrument to obtain a second tissue sample at the second sample location within the pattern.

Some implementations further comprise adjusting the pattern for the one or more samples to the first sample location or the second sample location after receiving the user input. In some implementations, adjusting the pattern is based on one or more anatomical features. In some implementations, the anatomical features comprise one or more blood vessels. In some implementations, adjusting the pattern comprises measuring an initial location of the distal portion of the instrument and fitting the pattern to the tissue site based on the initial location of the distal portion of the instrument.

In some implementations, fitting the pattern comprises calculating a route of the distal portion of the instrument from the initial location to the first sample location or the second sample location. In some implementations, fitting the pattern comprises adjusting one or more penetration depths, one or more sampling velocities, one or more sampling intervals, or one or more sampling forces of the instrument at the first sample location or the second sample location. In some implementations, adjusting the pattern comprises fitting the pattern to a shape of the tissue site. In some implementations, adjusting the pattern comprises fitting the pattern to a shape whose center is within the tissue site. In some implementations, adjusting the pattern comprises adjusting the pattern such that at least one sample location of the pattern corresponds to a center of the tissue site.

Some implementations further comprise adjusting movement of the distal portion of the instrument based on a respiration frequency of the patient when guiding the instrument to obtain the first tissue sample or the second tissue sample.

In some implementations, moving the distal portion of the instrument of the robotic medical system to the second position occurs after receiving a notification of collection of the first tissue sample at the first sample location.

Some implementations further comprise moving the distal portion of the instrument of the robotic medical system to a third position corresponding to a third sample location within the pattern; and guiding the instrument to obtain a third tissue sample at the third sample location within the pattern. In some implementations, moving the distal portion of the instrument of the robotic medical system to the third position occurs after receiving a notification of collection of the second tissue sample at the second sample location.

In some implementations, moving the distal portion of the instrument of the robotic medical system to the first position or the second position comprises: calculating at least one position of the distal portion of the instrument based on a data signal from a set of location sensors; and controlling movement of the instrument based on the calculated at least one position.

Some implementations further comprise actuating the instrument to obtain the first tissue sample from the first respective sample location within the pattern. Some implementations further comprise: actuating the instrument to obtain the second tissue sample from the second respective sample location within the pattern. Some implementations are performed by one or more hardware processors.

Still another aspect relates to a non-transitory computer readable storage medium having stored thereon instructions that, when executed, cause at least one computing device to at least: receive a pattern for one or more biopsy samples, the pattern comprising one or more biopsy positions arranged in at least two dimensions within a target tissue site of a patient; and move a distal portion of an instrument of the robotic medical system to one or more sampling positions that correspond to the one or more biopsy positions arranged in the at least two dimensional pattern.

In some implementations, the instructions, when executed, cause the at least one computing device to at least: calculate at least one position of the distal portion of the instrument based on a data signal from a set of location sensors; and controlling movement of the instrument based on the calculated at least one position. In some implementations, the instructions, when executed, cause the at least one computing device to at least: calculate a route of the distal portion of the instrument from an initial location to the one or more sampling positions.

In some implementations, the instructions, when executed, cause the at least one computing device to at least: calculate movement of a scope of the instrument according to the pattern; and move a distal portion of the scope to the one or more sampling positions. In some implementations, the instructions, when executed, cause the at least one computing device to at least: calculate movement of a collection device of the instrument according to the pattern; and move a collection device to the one or more sampling positions.

In some implementations, the instructions, when executed, cause the at least one computing device to at least: adjust the pattern for the one or more biopsy samples based on one or more anatomical features of the tissue site or a respiratory rate of the patient. In some implementations, the instructions, when executed, cause the at least one computing device to at least: adjust the pattern for the one or more biopsy samples based on one or more blood vessels within the tissue site.

In some implementations, the instructions, when executed, cause the at least one computing device to at least: measure an initial location of the distal portion of the instrument; and adjust the pattern for the one or more biopsy samples based on the initial location of the distal portion of the instrument.

In some implementations, the instructions, when executed, cause the at least one computing device to at least: fit the pattern to a shape of the tissue site. In some implementations, the instructions, when executed, cause the at least one computing device to at least: fit the pattern to a shape whose center is within the tissue site. In some implementations, the instructions, when executed, cause the at least one computing device to at least: adjust the pattern such that at least one sampling position of the pattern corresponds to a center of the tissue site.

In some implementations, the instructions, when executed, cause the at least one computing device to at least: adjust one or more penetration depths, one or more sampling velocities, one or more sampling intervals, or one or more sampling forces of the instrument at the one or more sampling positions.

In some implementations, the instructions, when executed, cause the at least one computing device to at least: actuate the distal portion of the instrument to obtain the one or more biopsy samples from the one or more sampling positions. In some implementations, the instructions, when executed, cause the at least one computing device to at least: receive one or more collection locations at which the instrument obtains the one or more biopsy samples; and adjust the pattern based on the one or more collection locations.

BRIEF DESCRIPTION OF THE DRAWINGS

The disclosed aspects will hereinafter be described in conjunction with the appended drawings and appendices, provided to illustrate and not to limit the disclosed aspects, wherein like designations denote like elements.

DETAILED DESCRIPTION

Introduction

Figure 1A:
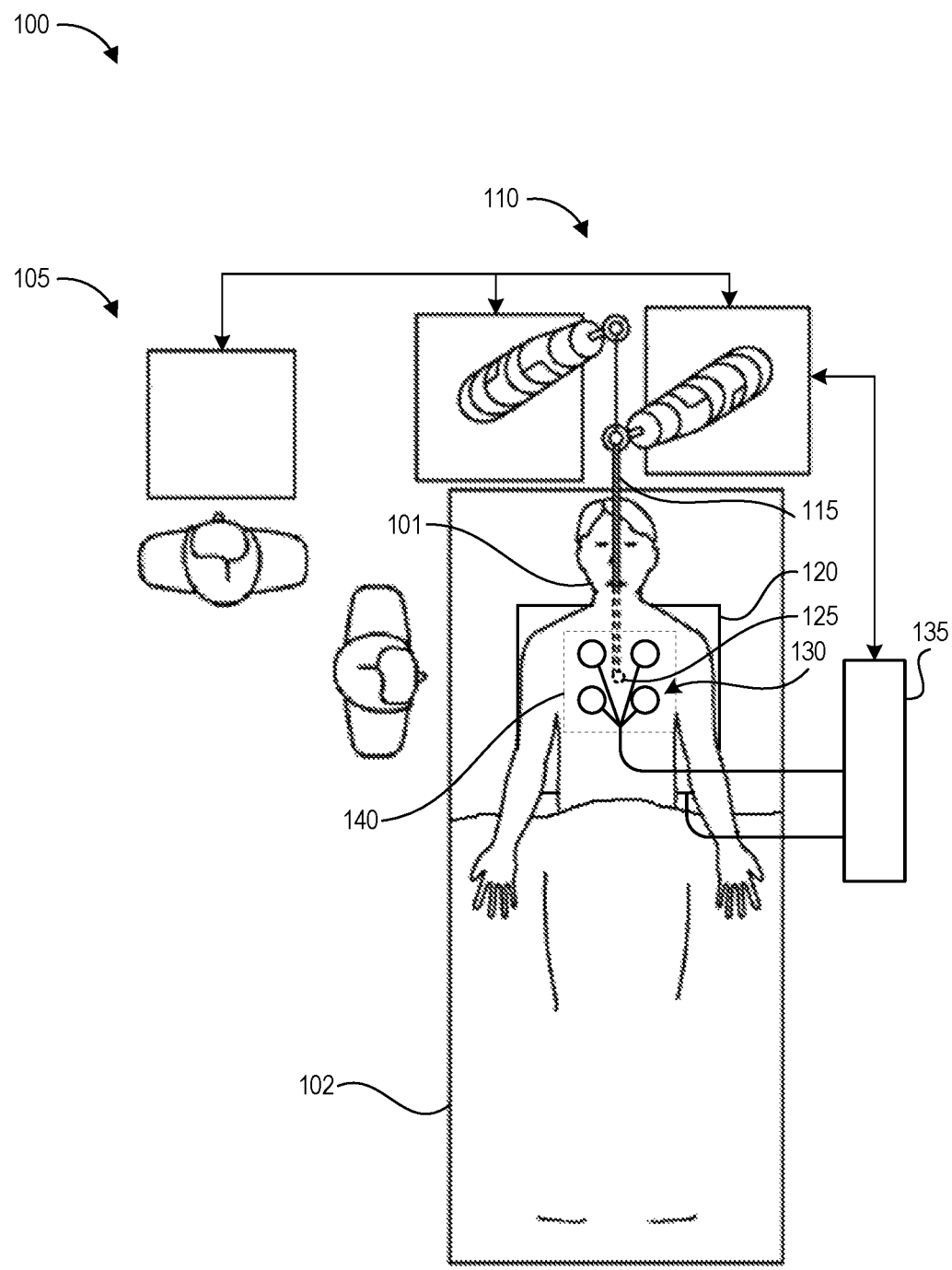
FIG. 1A illustrates an example operating environment for implementing an embodiment of a biopsy apparatus and method.

Embodiments of the disclosure relate to systems and techniques that guide a medical instrument to sample locations for biopsy in various target tissue sites (e.g., trachea of lung) by receiving a biopsy pattern including sample locations at which biopsy samples are collected and/or calculating movement of the medical instrument based on the sample locations within the biopsy pattern.

When a physician inserts a biopsy tool through a medical instrument to collect tissue samples (e.g., via bronchoscopy), the physician's ability to biopsy several different nearby locations in a reliable and systematic fashion may increase the quantity of materials collected and the likelihood of collecting tissue samples that can be used for diagnosis. In addition, the physician's ability to biopsy tissue samples in a specific pattern (e.g., a pre-defined pattern or a user-defined pattern) on a target tissue site may enable a strategic collection of biopsy samples from the target tissue site and increase the likelihood of collecting heterogeneous tissue samples. However, manual articulation of the medical instrument and/or manual biopsy may be limited by constraints in control, stability, and available degree of freedom of movement.

The disclosed systems and techniques can provide advantages for bronchoscopy biopsy guidance systems and other applications, including other types of endoscopic procedures for guided biopsy. In anatomy, a "lumen" may refer to the inner open space or cavity of an organ, as of an airway, a blood vessel, or an intestine. As used herein, a "luminal network" refers to an anatomical structure having at least one lumen leading towards a target tissue site, for example the airways of the lungs, the circulatory system, and the gastrointestinal system. Thus, although the present disclosure provides examples of biopsy guidance systems relating to bronchoscopy, it will be appreciated that the disclosed aspects are applicable to other medical systems for biopsy guidance. In addition, although the present disclosure provides examples of taking a biopsy samples at a target site, it will be appreciated that the disclosed aspects are also applicable to other medical procedures wherein movement of a medical instrument in a specific pattern (e.g., a pre-defined pattern or a user-defined pattern) is useful.

As used herein, "distal" refers to the end of a scope, instrument, or tool positioned closest to the patient during use, and "proximal" refers to the end of the scope, instrument, or tool positioned closest to the operator (e.g., a physician or robotic control system). Stated differently, the relative positions of components of the scope, instrument, tool, and/or the robotic system are described herein from the vantage point of the operator.

As used herein, the terms "about" or "approximately" refer to a range of measurements of a length, thickness, a quantity, time period, or other measurable values. Such range of measurements encompasses variations of +/−10% or less, preferably +/−5% or less, more preferably +/−1% or less, and still more preferably +/−0.1% or less, of and from the specified value, in so far as such variations are appropriate in order to function in the disclosed devices, systems, and techniques.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

Overview of Example Biopsy Guidance System

FIG. 1A illustrates an example operating environment 100 implementing one or more aspects of the disclosed biopsy systems and techniques. The operating environment 100 includes patient 101, a platform 102 supporting the patient 101, a surgical robotic system 110 guiding movement of endoscope 115, command center 105 for controlling operations of the surgical robotic system 110, electromagnetic (EM) controller 135, EM field generator 120, and EM sensors 125, 130. FIG. 1A also illustrates an outline of a region of a luminal network 140 within the patient 101, shown in more detail in FIG. 1B.

The surgical robotic system 110 can include one or more robotic arms for positioning and guiding movement of endoscope 115 through the luminal network 140 of the patient 101 and, in some cases, actuating a collection device (e.g., a biopsy needle, brush, forceps, or the like). Command center 105 can be communicatively coupled to the surgical robotic system 110 for receiving position data and/or providing control signals from a user. As used herein, "communicatively coupled" refers to any wired and/or wireless data transfer mediums, including but not limited to a wireless wide area network (WWAN) (e.g., one or more cellular networks), a wireless local area network (WLAN) (e.g., configured for one or more standards, such as the IEEE 802.11 (Wi-Fi)), Bluetooth, data transfer cables, and/or the like. The surgical robotic system 110 is discussed in more detail with respect to FIG. 1C, and the command center 105 is discussed in more detail with respect to FIG. 2.

The endoscope 115 may be a tubular and flexible surgical instrument that is inserted into the anatomy of a patient to capture images of the anatomy (e.g., body tissue, target tissue site) and provide a working channel for insertion of other medical instruments to a target tissue site. In some implementations, the endoscope 115 can be a bronchoscope. The endoscope 115 can include one or more location sensors at its distal end. The one or more location sensors may comprise imaging devices (e.g., cameras or other types of optical sensors), ultrasound transducers, X-ray devices (e.g., X-ray image intensifiers, X-ray imaging devices, and fluoroscopy devices) and/or EM sensors. The imaging devices may include one or more optical components such as an optical fiber, fiber array, photosensitive substrate, and/or lens(es). The optical components move along with the tip of the endoscope 115 such that movement of the tip of the endoscope 115 results in corresponding changes to the field of view of the images captured by the imaging devices. The distal end of the endoscope 115 can be provided with one or more ultrasound transducers (e.g., radial-scanning or linear-scanning ultrasound transducers) or X-ray devices configured to produce images of the anatomy (e.g., body tissue). The images of the anatomy produced from the imaging devices, the ultrasound transducers, and/or the X-ray devices may be used to identify position and/or orientation of the distal end of the endoscope 115. In some embodiments, one or more models of the anatomy of the patient may be used together with the images of the anatomy to identify position and/or orientation of the distal end of the endoscope 115. As an example, a preoperative procedure can be performed to take CT scans of a patient's lungs, and a computing system can use data from these scans to build a 3D model of the lungs of the patient. Such a model can provide 3D information about the structure and connectivity of the lung luminal network, including the topography and/or diameters of patient airways in some examples. Some CT scans are performed at breath-hold so that the patient's airways are expanded to their full diameter. Then, this model of the luminal network may be used in conjunction with the images from the one or more location sensors at the distal end of the endoscope 115 to determine position and/or orientation of the distal end.

In addition, the distal end of the endoscope 115 can be provided with one or more EM sensors for tracking the position of the distal end within an EM field generated around the luminal network 140. The distal end of the endoscope 115 is further described with reference to FIG. 3 below.

EM controller 135 can control EM field generator 120 to produce a varying EM field. The EM field can be time-varying and/or spatially varying, depending upon the embodiment. The EM field generator 120 can be an EM field generating board in some embodiments. Some embodiments of the disclosed biopsy guidance systems can use an EM field generator board positioned between the patient and the platform 102 supporting the patient, and the EM field generator board can incorporate a thin barrier that minimizes any tracking distortions caused by conductive or magnetic materials located below it. In other embodiments, an EM field generator board can be mounted on a robotic arm, for example similar to those shown in surgical robotic system 110, which can offer flexible setup options around the patient.

An EM spatial measurement system incorporated into the command center 105, surgical robotic system 110, and/or EM controller 135 can determine the location of objects within the EM field that are embedded or provided with EM sensor coils, for example EM sensors 125, 130. When an EM sensor is placed inside a controlled, varying EM field as described herein, voltages are induced in the sensor coils. These induced voltages can be used by the EM spatial measurement system to calculate the position and/or orientation of the EM sensor and thus the object having the EM sensor. As the magnetic fields are of a low field strength and can safely pass through human tissue, location measurement of an object is possible without the line-of-sight constraints of an optical spatial measurement system.

EM sensor 125 can be coupled to a distal end of the endoscope 115 in order to track its location within the EM field. The EM field is stationary relative to the EM field generator, and a coordinate frame of a 3D model of the luminal network can be mapped to a coordinate frame of the EM field.

Figure 1B:
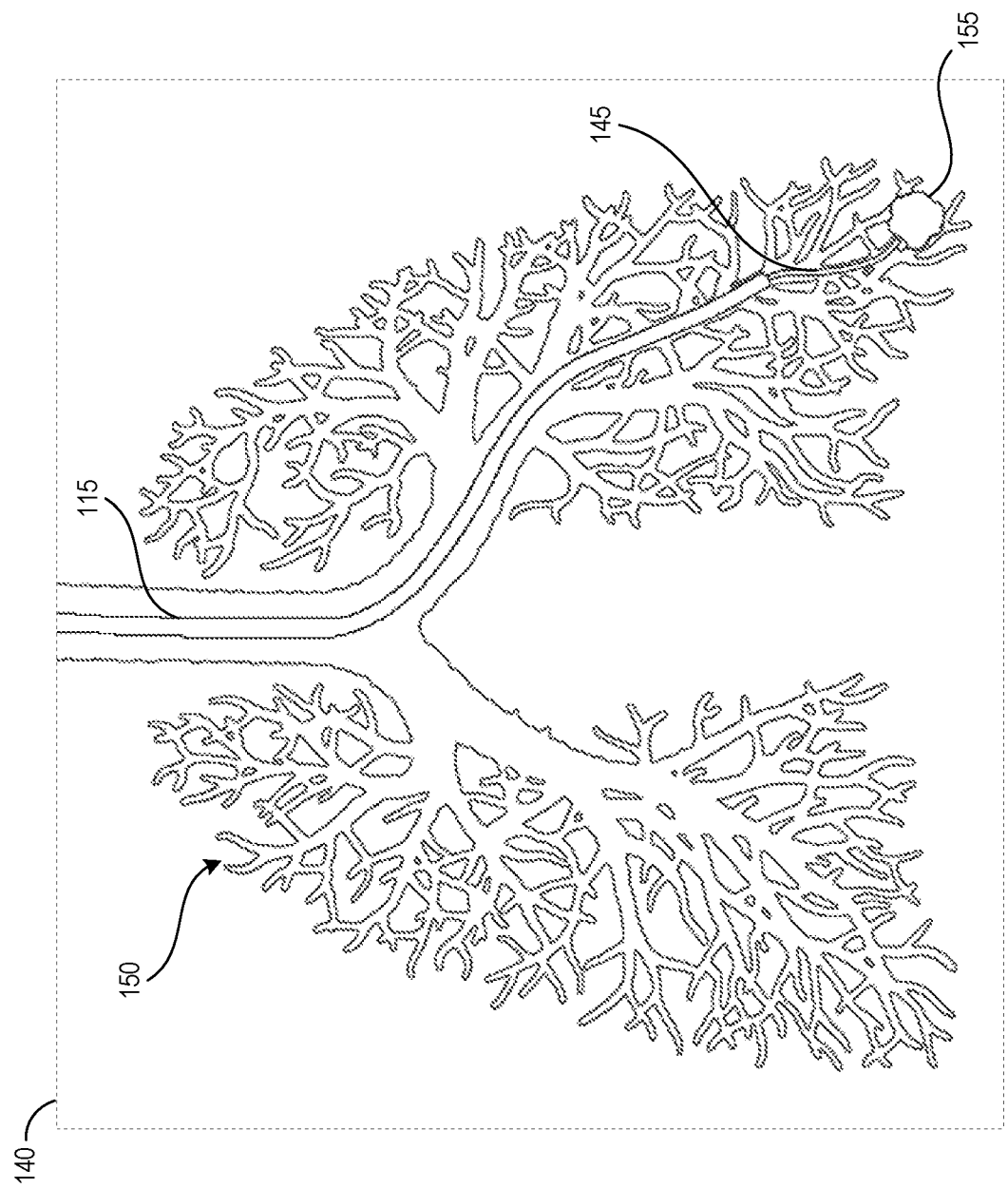
FIG. 1B illustrates an example luminal network navigated for biopsy in the environment of FIG. 1A.

FIG. 1B illustrates an example luminal network 140 that can be navigated for biopsy in the operating environment 100 of FIG. 1A. The luminal network 140 includes the branched structure of the airways 150 of the patient and a nodule 155 (or lesion) that can be accessed as described herein for biopsy. As illustrated, the nodule 155 is located at the periphery of the airways 150. The endoscope 115 has a first diameter and thus its distal end is not able to be positioned through the smaller-diameter airways around the nodule 155. Accordingly, a steerable catheter 145 extends from the working channel of the endoscope 115 the remaining distance to the nodule 155. The steerable catheter 145 may have a lumen through which instruments, for example biopsy needles, cytology brushes, and/or tissue sampling forceps, can be passed to the target tissue site of nodule 155. In such implementations, both the distal end of the endoscope 115 and the distal end of the steerable catheter 145 can be provided with EM sensors for tracking their position within the airways 150. In other embodiments, the overall diameter of the endoscope 115 may be small enough to reach the periphery without the steerable catheter 145, or may be small enough to get close to the periphery (e.g., within 2.5-3 cm) to deploy medical instruments through a non-steerable catheter (not illustrated). The medical instruments deployed through the endoscope 115 may be equipped with EM sensors.

In some embodiments, a 2D display of a 3D luminal network model as described herein, or a cross-section of a 3D model, can resemble FIG. 1B.

Figure 1C:
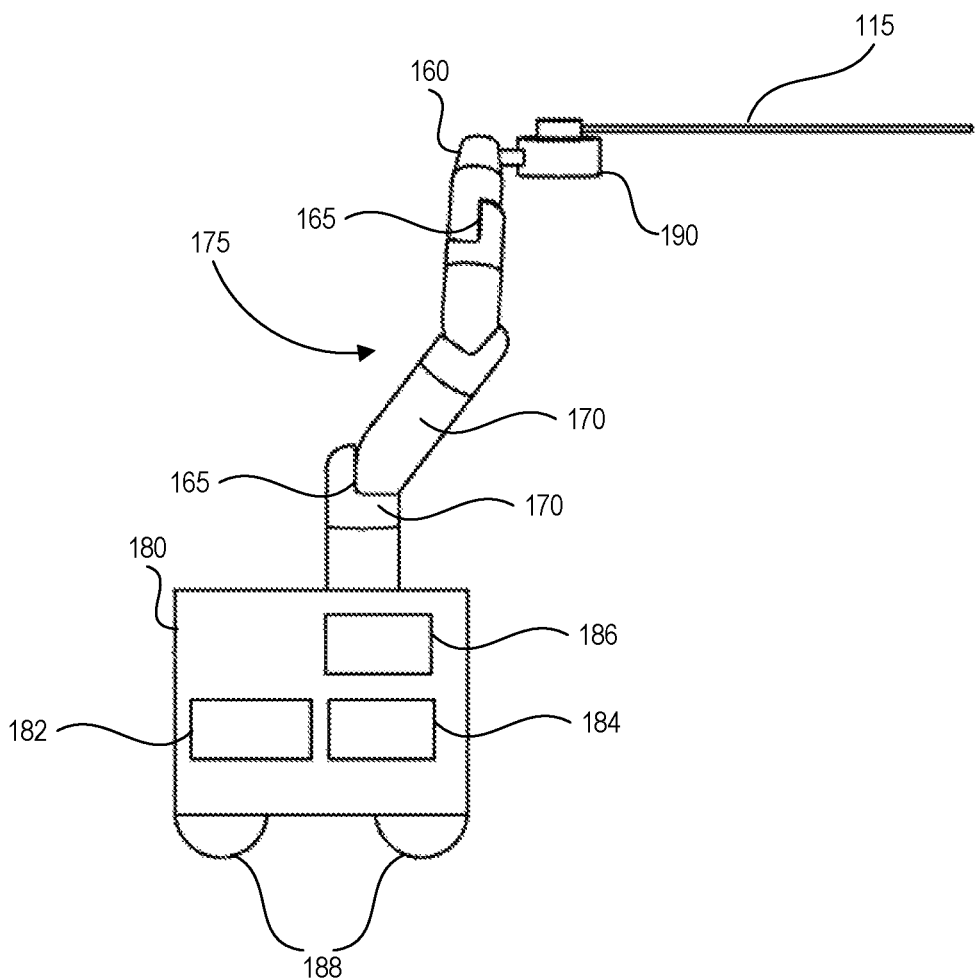
FIG. 1C illustrates an example robotic arm for guiding an instrument to sample locations for biopsy in the luminal network of FIG. 1B.

FIG. 1C illustrates an example robotic arm 175 of a surgical robotic system 110 for guiding instrument movement in through the luminal network 140 of FIG. 1B. The surgical robotic system 110 includes a base 180 coupled to one or more robotic arms, e.g., robotic arm 175. The robotic arm 175 includes multiple arm segments 170 coupled at joints 165, which provide the robotic arm 175 multiple degrees of freedom. As an example, one implementation of the robotic arm 175 can have seven degrees of freedom corresponding to seven arm segments. In some embodiments, the robotic arm 175 includes set up joints that use a combination of brakes and counter-balances to maintain a position of the robotic arm 175. The counter-balances may include gas springs and/or coil springs. The brakes, e.g., fail safe brakes, may include mechanical and/or electrical components. Further, the robotic arm 175 may be a gravity-assisted passive support type robotic arm.

The robotic arm 175 may be coupled to an instrument device manipulator (IDM) 190 using a mechanism changer interface (MCI) 160. The IDM 190 can be removed and replaced with a different type of IDM, for example, a first type of IDM configured to manipulate an endoscope or a second type of IDM configured to manipulate a laparoscope. The MCI 160 includes connectors to transfer pneumatic pressure, electrical power, electrical signals, and optical signals from the robotic arm 175 to the IDM 190. The MCI 160 can be a set screw or base plate connector. The IDM 190 manipulates surgical instruments, for example the endoscope 115 using techniques including direct drive, harmonic drive, geared drives, belts and pulleys, magnetic drives, and the like. The MCI 160 is interchangeable based on the type of IDM 190 and can be customized for a certain type of surgical procedure. The robotic arm 175 can include joint level torque sensing capabilities (e.g., using one or more torque sensors positioned at or near the joints 165) and a wrist at a distal end.

Robotic arm 175 of the surgical robotic system 110 can manipulate the endoscope 115 using elongate movement members. The elongate movement members may include pull wires, also referred to as pull or push wires, cables, fibers, or flexible shafts. For example, the robotic arm 175 can actuate multiple pull wires coupled to the endoscope 115 to deflect the tip of the endoscope 115. The pull wires may include both metallic and non-metallic materials, for example stainless steel, Kevlar, tungsten, carbon fiber, and the like. The endoscope 115 may exhibit nonlinear behavior in response to forces applied by the elongate movement members. The nonlinear behavior may be based on stiffness and compressibility of the endoscope 115, as well as variability in slack or stiffness between different elongate movement members.

The base 180 can be positioned such that the robotic arm 175 has access to perform or assist with a surgical procedure on a patient, while a user such as a physician may control the surgical robotic system 110 from the comfort of the command console. In some embodiments, the base 180 may be coupled to a surgical operating table or bed (e.g., a platform 102) for supporting the patient. The base 180 can be communicatively coupled to the command console 105 shown in FIG. 1A.

The base 180 can include a source of power 182, pneumatic pressure 186, and control and sensor electronics 184—including components such as a central processing unit, data bus, control circuitry, and memory—and related actuators such as motors to move the robotic arm 175. As used herein, the term "actuator" may refer to a mechanism for physically adjusting the position and/or orientation of the robotic arm 175. The electronics 184 can implement the biopsy guidance techniques described herein. The electronics 184 in the base 180 may also process and transmit control signals communicated from the command console. In some embodiments, the base 180 includes wheels 188 to transport the surgical robotic system 110 and wheel locks/brakes (not shown) for the wheels 188. Mobility of the surgical robotic system 110 helps accommodate space constraints in a surgical operating room as well as facilitate appropriate positioning and movement of surgical equipment. Further, the mobility allows the robotic arm 175 to be configured such that the robotic arm 175 does not interfere with the patient, physician, anesthesiologist, or any other equipment. During procedures, a user may control the robotic arm 175 using control devices, for example the command console.

Figure 2:
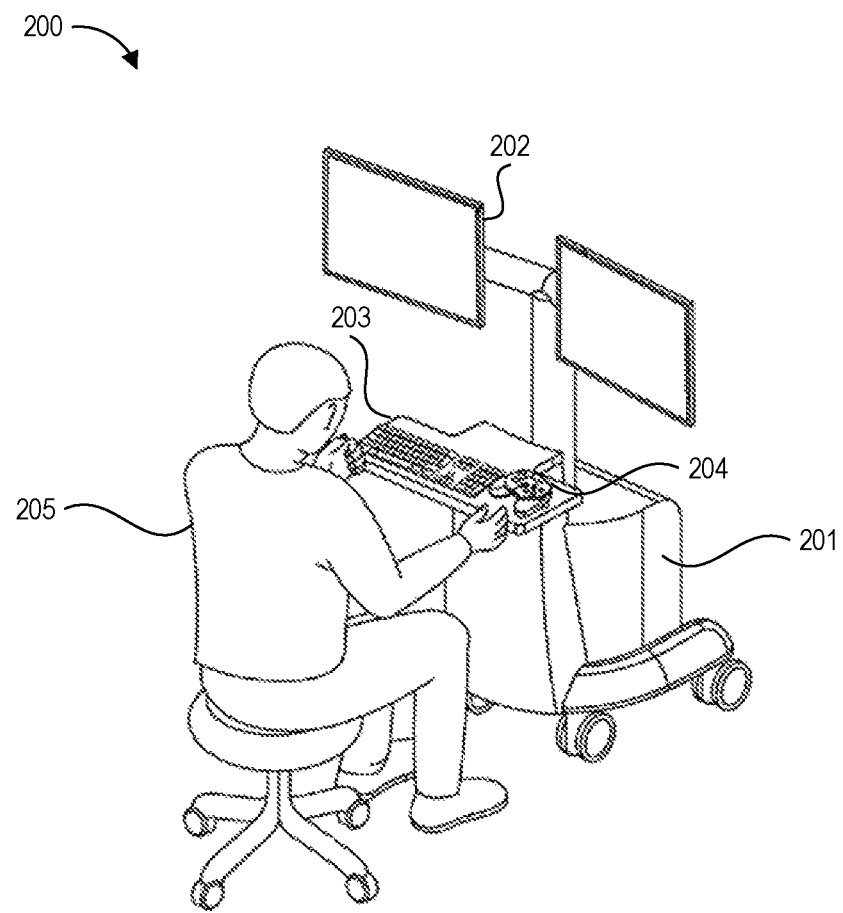
FIG. 2 illustrates an example command console for an example surgical robotic system, according to one embodiment.

FIG. 2 illustrates an example command console 200 that can be used, for example, as the command console 105 in the example operating environment 100. The command console 200 includes a console base 201, display modules 202, e.g., monitors, and control modules, e.g., a keyboard 203 and joystick 204. In some embodiments, one or more of the command console 200 functionality may be integrated into a base 180 of the surgical robotic system 110 or another system communicatively coupled to the surgical robotic system 110. A user 205, e.g., a physician, remotely controls the surgical robotic system 110 from an ergonomic position using the command console 200.

The console base 201 may include a central processing unit, a memory unit, a data bus, and associated data communication ports that are responsible for interpreting and processing signals such as camera imagery and tracking sensor data, e.g., from the endoscope 115 shown in FIGS. 1A-1C. In some embodiments, both the console base 201 and the base 180 perform signal processing for load-balancing. The console base 201 may also process commands and instructions provided by the user 205 through the control modules 203 and 204. In addition to the keyboard 203 and joystick 204 shown in FIG. 2, the control modules may include other devices, for example, computer mice, trackpads, trackballs, control pads, controllers such as handheld remote controllers, and sensors (e.g., motion sensors or cameras) that capture hand gestures and finger gestures. A controller can include a set of user inputs (e.g., buttons, joysticks, directional pads, etc.) mapped to an operation of the instrument (e.g., articulation, driving, water irrigation, etc.).

Using the command console 200, the user 205 can input a biopsy pattern comprising one or more sample locations at which biopsy samples are collected. In some embodiments, the user 205 using the command console 200 may input one or more commands to access the biopsy pattern or one or more commands to display the biopsy pattern (e.g., via display modules 202). In another embodiment, the user 205 using the command console 200 may input one or more commands to calculate movement of a medical instrument (e.g., endoscope 115, robotic arm 175) toward the sample locations. In yet another embodiments, the user 205 using the command console 200 may input one or more commands to move the instrument toward the sample locations.

The user 205 can control a surgical instrument such as the endoscope 115 using the command console 200 in a velocity mode or position control mode. In velocity mode, the user 205 directly controls pitch and yaw motion of a distal end of the endoscope 115 based on direct manual control using the control modules. For example, movement on the joystick 204 may be mapped to yaw and pitch movement in the distal end of the endoscope 115. The joystick 204 can provide haptic feedback to the user 205. For example, the joystick 204 may vibrate to indicate that the endoscope 115 cannot further translate or rotate in a certain direction. The command console 200 can also provide visual feedback (e.g., pop-up messages) and/or audio feedback (e.g., beeping) to indicate that the endoscope 115 has reached maximum translation or rotation. The haptic and/or visual feedback can also be provided due to the system operating in a safety mode during patient expiration as described in more detail below.

In position control mode, the command console 200 uses a three-dimensional (3D) map of a patient luminal network and input from location sensors as described herein to control a surgical instrument, e.g., the endoscope 115. The command console 200 provides control signals to robotic arms 175 of the surgical robotic system 110 to manipulate the endoscope 115 to a target location. Due to the reliance on the 3D map, position control mode may require accurate mapping of the anatomy of the patient.

In some embodiments, users 205 can manually manipulate robotic arms 175 of the surgical robotic system 110 without using the command console 200. During setup in a surgical operating room, the users 205 may move the robotic arms 175, endoscope 115 (or endoscopes), and other surgical equipment to access a patient. The surgical robotic system 110 may rely on force feedback and inertia control from the users 205 to determine appropriate configuration of the robotic arms 175 and equipment.

The displays 202 may include one or more user interface screens, such as electronic monitors (e.g., LCD displays, LED displays, touch-sensitive displays), virtual reality viewing devices, e.g., goggles or glasses, and/or other display devices. In some embodiments, the display modules 202 are integrated with the control modules, for example, as a tablet device with a touchscreen. In some embodiments, one of the displays 202 may display a virtual representation of the biopsy pattern or one or more sample locations within the biopsy pattern. In some embodiments, one of the displays 202 can display a 3D model of the patient's luminal network and virtual biopsy information (e.g., a virtual representation of the biopsy pattern in the target tissue site or a virtual representation of paths of the end of the endoscope toward sample locations of the biopsy pattern within the model based on EM sensor position) while the other of the displays 202 can display image information received from the camera or another sensing device at the end of the endoscope 115. In some implementations, the user 205 can both view data and input commands to the surgical robotic system 110 using the integrated displays 202 and control modules. The displays 202 can display 2D renderings of 3D images and/or 3D images using a stereoscopic device, e.g., a visor or goggles. The 3D images provide an "endo view" (i.e., endoscopic view), which is a computer 3D model illustrating the anatomy of a patient. The "endo view" provides a virtual environment of the patient's interior and an expected location of an endoscope 115 inside the patient. A user 205 compares the "endo view" model to actual images captured by a camera to help mentally orient and confirm that the endoscope 115 is in the correct—or approximately correct—location within the patient. The "endo view" provides information about anatomical structures, e.g., the shape of airways, circulatory vessels, or an intestine or colon of the patient, around the distal end of the endoscope 115. The display modules 202 can simultaneously display the 3D model and CT scans of the anatomy the around distal end of the endoscope 115. Further, the display modules 202 may overlay the already determined paths of the distal end of the endoscope 115 on the 3D model and CT scans.

In some embodiments, a model of the endoscope 115 is displayed with the 3D models to help indicate a status of a surgical procedure. For example, the CT scans identify a nodule in the anatomy where a biopsy may be necessary. During operation, the display modules 202 may show a reference image captured by the endoscope 115 corresponding to the current location of the endoscope 115. The display modules 202 may automatically display different views of the model of the endoscope 115 depending on user settings and a particular surgical procedure. For example, the display modules 202 show an overhead fluoroscopic view of the endoscope 115 as the endoscope 115 approaches an operative region of a patient and sample locations within the biopsy pattern.

Figure 3:
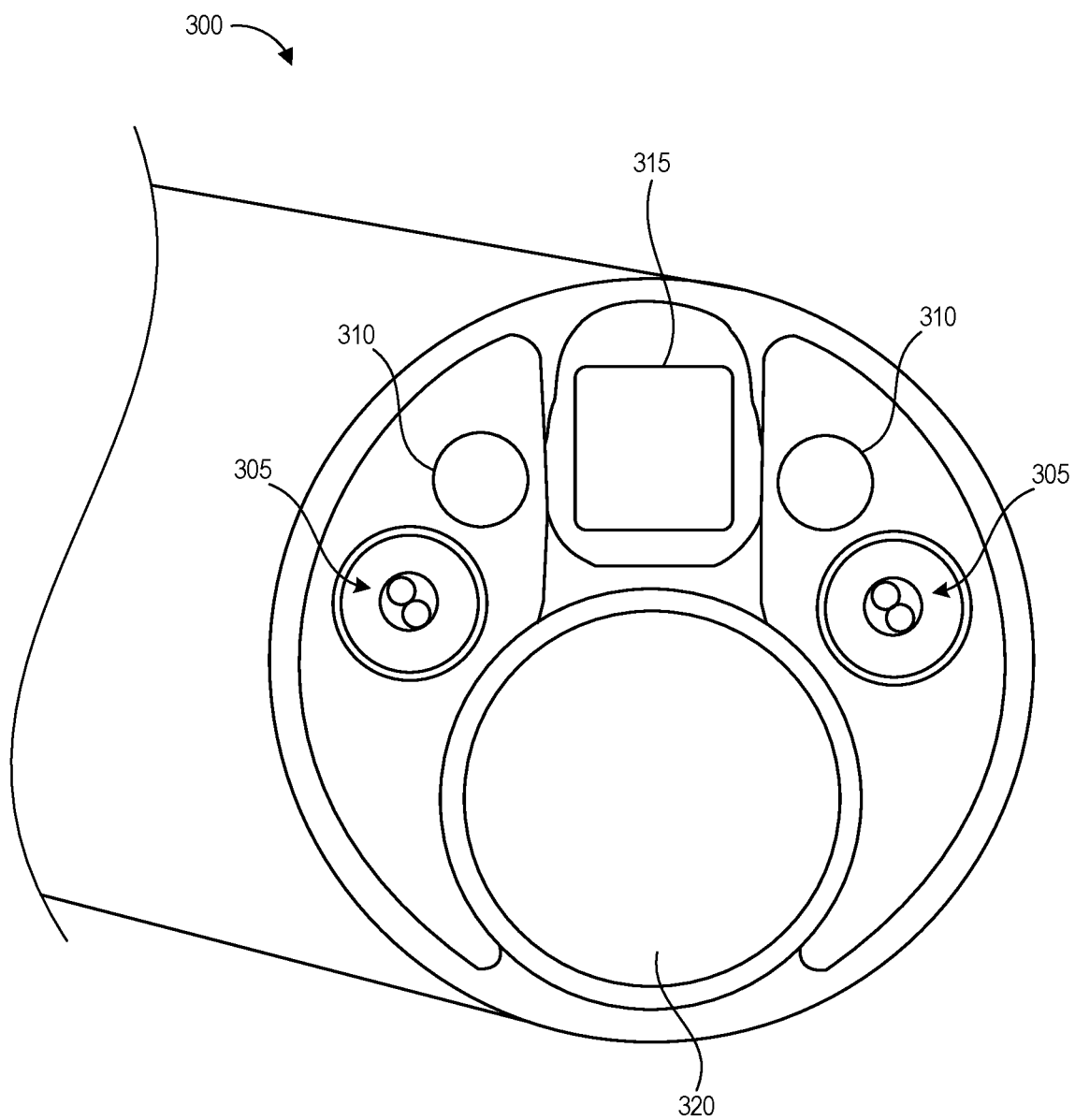
FIG. 3 illustrates an distal end of example endoscope having imaging capabilities as described herein.

FIG. 3 illustrates the distal end 300 of an example endoscope having imaging and EM sensing capabilities as described herein, for example the endoscope 115 of FIGS. 1A-1C. As shown in FIG. 3, the distal end 300 of the endoscope includes an imaging device 315, illumination sources 310, and may include ends of EM sensor coils 305. The distal end 300 further includes an opening to a working channel 320 of the endoscope through which surgical instruments, such as biopsy needles, cytology brushes, and forceps, may be inserted along the endoscope shaft, allowing access to the area near the endoscope tip.

The illumination sources 310 provide light to illuminate a portion of an anatomical space. The illumination sources can each be one or more light-emitting devices configured to emit light at a selected wavelength or range of wavelengths. The wavelengths can be any suitable wavelength, for example visible spectrum light, infrared light, x-ray (e.g., for fluoroscopy), to name a few examples. In some embodiments, illumination sources 310 can include light-emitting diodes (LEDs) located at the distal end 300. In some embodiments, illumination sources 310 can include one or more fiber optic fibers extending through a length of the endoscope to transmit light through the distal end 300 from a remote light source, for example an X-ray generator. Where the distal end 300 includes multiple illumination sources 310 these can each be configured to emit the same or different wavelengths of light as one another.

The imaging device 315 can include any photosensitive substrate or structure configured to convert energy representing received light into electric signals, for example a charge-coupled device (CCD) or complementary metal-oxide semiconductor (CMOS) image sensor. Some examples of imaging device 315 can include one or more optical fibers, for example a fiber optic bundle, configured to transmit an image from the distal end 300 of the endoscope to an eyepiece and/or image sensor at the proximal end of the endoscope. Imaging device 315 can additionally include one or more lenses and/or wavelength pass or cutoff filters as required for various optical designs. The light emitted from the illumination sources 310 allows the imaging device 315 to capture images of the interior of a patient's luminal network. These images can then be transmitted as individual frames or series of successive frames (e.g., a video) to a computer system such as command console 200 for processing as described herein.

Electromagnetic coils 305 located on the distal end 300 may be used with an electromagnetic tracking system to detect the position and/or orientation of the distal end 300 of the endoscope while it is disposed within an anatomical system. In some embodiments, the coils 305 may be angled to provide sensitivity to electromagnetic fields along different axes, giving the disclosed navigational systems the ability to measure a full 6 degrees of freedom: three positional and three angular. In other embodiments, only a single coil may be disposed on or within the distal end 300 with its axis oriented along the endoscope shaft of the endoscope. Due to the rotational symmetry of such a system, it is insensitive to roll about its axis, so only 5 degrees of freedom may be detected in such an implementation.

Figure 4:
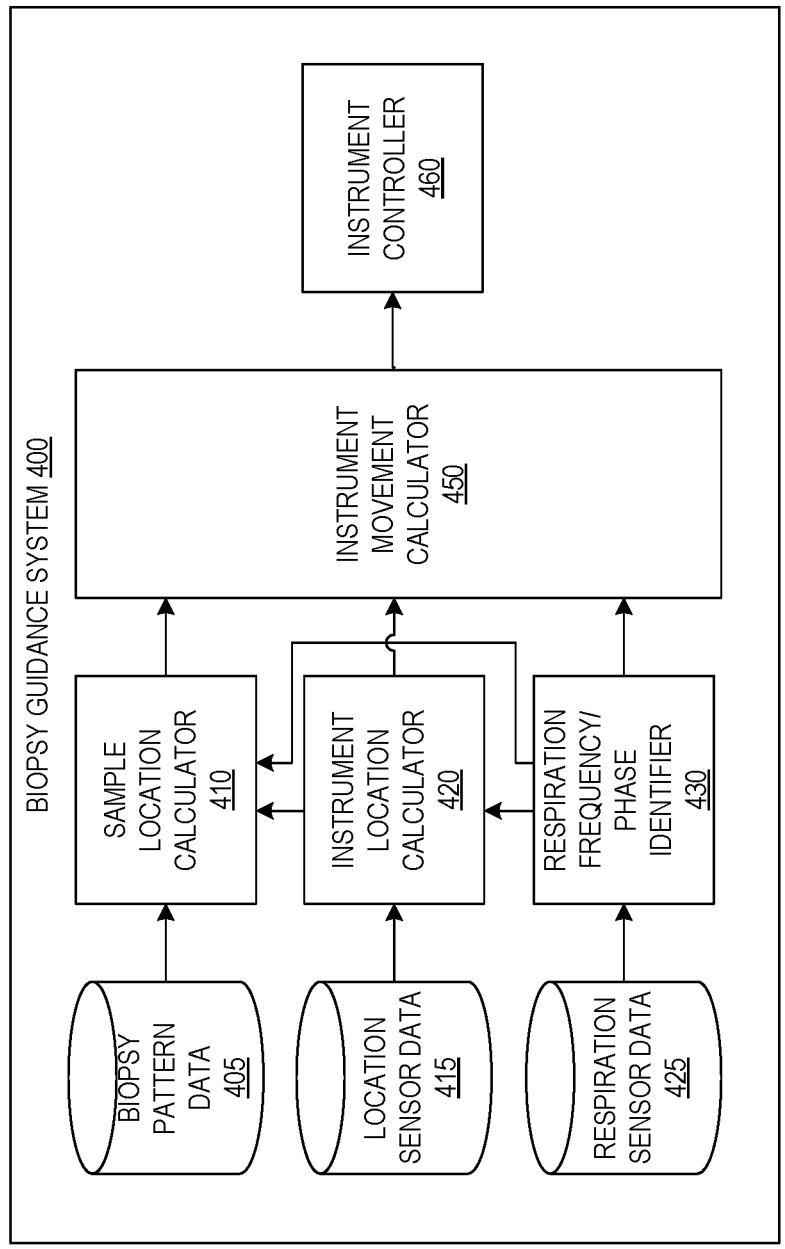
FIG. 4 depicts a schematic block diagram of an embodiment of a biopsy guidance system as described herein.

FIG. 4 illustrates a schematic block diagram of an example biopsy guidance system 400 as described herein. As described in more detail below, the system 400 combines and analyzes data from a number of different sources during a medical procedure to provide an estimation of the movement, location, and/or orientation information of a medical instrument (e.g., the endoscope 115) within the anatomical structures of the patient and, more specifically, to determine movements of the medical instrument (e.g., the distal end of the medical instrument and/or a sample collection device of the medical instrument) toward sample locations within the biopsy pattern at which biopsy takes place. The system 400 includes a number of data repositories including biopsy pattern data repository 405 and location sensor data repository 415. In some embodiments, the system 400 may include respiration sensor data repository 425. Though shown separately in FIG. 4 for purposes of clarity in the discussion below, it will be appreciated that some or all of the data repositories can be stored together in a single memory or set of memories. The system 400 also includes a number of processing modules including sample location calculator 410 and instrument location calculator 420. In some embodiments, the system 400 may include respiration frequency and/or phase identifier 430. Each module can represent a set of computer-readable instructions, stored in a memory, and one or more processors configured by the instructions for performing the features described below together. The biopsy guidance system 400 can be implemented as one or more data storage devices and one or more hardware processors, for example in the control and sensor electronics 184 and/or console base 201 described above. While the biopsy guidance system 400 is described as using data from a number of different sources, it should be appreciated that biopsy guidance system 400 may use more, less and/or different data sources than what is shown in FIG. 4.

Biopsy pattern data repository 405 is a data storage device that stores biopsy pattern data that characterizes one or more biopsy patterns. Biopsy pattern data repository 405 may include one or more sample locations within the biopsy patterns at which biopsy samples are to be collected. The one or more sample locations may be arranged in at least two dimensions. In an example embodiment, the sample locations can be stored as a tuple in the form of (x, y), where x and y represent the two dimensional coordinates of the one or more sample locations with respect to the distal end of the medical instrument (e.g., endoscope 115) on a plane perpendicular to a longitudinal axis of the distal end of the medical instrument. In another example, the sample locations of the biopsy pattern data can be stored as a tuple in the form of (x, y, z), where x, y, and z represent the coordinates of the one or more sample locations in a three dimensional coordinates. In some embodiments, the biopsy pattern data may characterize a shape and/or a center location of the biopsy pattern. For example, the biopsy pattern may comprise one or more sample locations arranged in a circle or a grid. In other embodiments in which a collection device of the medical instrument is robotically controlled, biopsy pattern data may include data characterizing one or more penetration depths, one or more sampling velocities, one or more sampling intervals, or one or more sampling forces of the medical instrument at the one or more sample locations.

The biopsy patterns characterized by the biopsy pattern data may be selected or modified by a user. In an example embodiment, the user is capable of selecting the location of the biopsy pattern in the target tissue site (e.g., a nodule or lesion to biopsy) by interfacing with a computer display that can show a representation of an anatomical model of the target tissue site (e.g., 3D model), such as by clicking with a mouse or touching a touchscreen. In another example, the user is capable of selecting a shape or a center location of the biopsy patterns. In some embodiments, the biopsy patterns may be identified programmatically by analysis of the anatomical model and the identified target tissue site to derive one or more biopsy patterns adapted to the target tissue site (e.g., a biopsy pattern fit to the shape of the target tissue site). The automatically-identified biopsy patterns may be modified by a physician.

Location sensor data repository 415 is a data storage device that stores location sensor data that characterizes positions and/or orientations of the distal end of the medical instrument (e.g., the endoscope 115). Positions and/or orientations of the distal end of the medical instrument may be determined by data from one or more location sensors (e.g., EM sensors, imaging devices, ultrasound transducers, or X-ray devices) and/or robotic position data. In embodiments in which the medical instrument include one or more EM sensors (e.g., EM sensor 125 and EM sensor coils 305) at the distal, data from the EM sensors can be used to identify positions and/or orientations of the sensor within the EM field. The location sensor data for an EM sensor can be stored as a tuple in the form of $(x, y, z, t_n)$, where x, y, and z represent the coordinates of the sensor in the EM field at time $t_n$. Some embodiments may further include roll, pitch, and yaw of the instrument in the EM sensor tuple. The location sensor data repository 415 can store a number of such tuples for each endoscope-based sensor corresponding to a number of different times. In embodiments in which the medical instrument include one or more imaging devices (e.g., imaging device 315 or camera), one or more ultrasound transducers, and/or one or more X-ray devices, the image data can be discrete images or series of image frames in a video sequence in various embodiments.

Robotic position data is data received from surgical robotic system 110, for example data related to physical movement of the medical instrument or part of the medical instrument (e.g., the instrument tip or distal end) by the surgical robotic system 110 within anatomical structures of the patient. Example robotic position data may include, e.g., command data instructing the instrument tip to reach a specific anatomical site and/or change its orientation (e.g., with a specific pitch, roll, yaw, insertion, and retraction for one or both of a leader and a sheath of an endoscopic instrument) within the anatomical structures of the patient, insertion data representing insertion movement of the part of the medical instrument (e.g., the instrument tip or sheath), IDM data (e.g., data from IDM 190), and mechanical data representing mechanical movement of an elongate member of the medical instrument, such as, for example, motion of one or more pull wires, tendons or shafts of the endoscope that drive the actual movement of the endoscope within the anatomical structures. Robotic position data may be tracked by one or more controllers of the distal end of the medical instrument (e.g., robotic arm 175).

In some embodiments, the system 400 may include respiration sensor data repository 425. Respiration sensor data repository 425 is a data storage device that stores respiration sensor data derived from a respiration sensor. The respiratory sensor can comprise EM sensor(s) 130, an acoustic respiratory sensor, an image sensor having a field of view positioned to capture images of the luminal network, and ventilator inflation/deflation information. In some embodiments, the respiratory sensor can comprise a number of EM sensors 130 and the data in the respiration sensor data repository 405 can include, for each sensor, time-dependent position data representing the positions of the sensor in the EM field over time. For example, respiration sensor data for each sensor can be stored as a tuple in the form of $(x, y, z, t_n)$ where x, y, and z represent the coordinates of the sensor in the EM field at time $t_n$. The respiration sensor data repository 425 can store a number of such tuples for each sensor corresponding to a number of different times. The respiration sensor data can be particularly useful in embodiments in which the endoscope 115 is a bronchoscope and the biopsy samples are to be taken in the lung.

Sample location calculator 410 is a module configured to receive data from the biopsy pattern data repository 405 and additionally from the location sensor data 415 and/or the respiration sensor data 425 in some embodiments, and analyze such data to calculate one or more sample locations within the biopsy pattern. In some embodiments, sample location calculator 410 may be configured to determine the sample locations within the biopsy patterns based on one or more inputs of a user using a user input device (e.g., command console 200). For example, the user inputs may include sample locations, penetration depths, sampling velocities, sampling intervals, sampling forces at the sample locations, shape of the biopsy pattern, and/or center location of the biopsy pattern as described above. In other embodiments, sample location calculator 410 may be further configured to adjust the sample locations within the biopsy patterns based on anatomical features of the target tissue (e.g., blood vessel network). In an example embodiment, sample location calculator 410 may adjust the biopsy pattern to avoid blood vessels within the blood vessel network near the target tissue site. In an example embodiment, sample location calculator 410 may adjust the biopsy pattern to fit to a shape of the tissue site. In another example, sample location calculator 410 may adjust the biopsy pattern to arrange in a shape whose center is within the tissue site. In yet another example, sample location calculator 410 may adjust the biopsy pattern such that at least one of the sample locations within the biopsy pattern corresponds to a center of the tissue site. In an example embodiment, after the medical instrument collect one or more biopsy samples, the sample location calculator 410 may be configured to adjust the one or more sample locations within the biopsy pattern based on actual locations in which the biopsy samples are collected as detected by movement of the distal end of the medical instrument (e.g., by the location sensors described above). In other embodiments, sample location calculator 410 may be further configured to adjust the sample locations within the biopsy patterns based on one or more user inputs from a user.

Instrument location calculator 420 is a module that receives data from the location sensor data repository 415 and use such data to determine the location and/or orientation of the distal end of the medical instrument (e.g., the endoscope). For example, the instrument location calculator 420 may be configured to translate data from one or more location sensors into 3D model coordinates and/or orientations of the distal end of the medical instrument.

In some embodiments, one or more models of the anatomy of the patient (e.g., target tissue site) described above may be used with data from the location data repository 415 to identify position and/or orientation of the distal end of the medical instrument. For example, a preoperative procedure can be performed to take CT scans of an anatomy of a patient's target tissue site, and a computing system can use data from these scans to build a 3D model of the anatomy. Such a model can provide 3D information about the structure and connectivity of the target tissue site. Then, a process known as "registration," which finds a geometric transformation that aligns one or more objects between different coordinate systems, may be conducted to perform a geometric transformation from the coordinate frame of the EM field generator 120 to the coordinate frame of the model (e.g., a coordinate frame of the preoperative model generated by the CT scans). The registration process is described in U.S. application Ser. No. 15/268,238, filed Sep. 17, 2016, titled "Navigation of Tubular Networks," the disclosure of which is hereby incorporated by reference. Data to perform the geometric transformation (e.g., locations of the one or more objects in different coordinate systems), also referred to as registration data, may updated continually or periodically in some implementations.

In embodiments in which the medical instrument includes one or more EM sensors at its distal end, the instrument location calculator 420 may be configured to translate EM sensor coordinates into 3D model coordinates. The instrument location calculator 420 calculates an initial position of the EM sensor relative to the position of the EM field generator. This position also corresponds to a location within the 3D model. In order to translate the initial position of the EM sensor from the EM coordinate frame into the model coordinate frame, the instrument location calculator 420 can access the mapping between the EM coordinate frame and the model coordinate frame (e.g., registration data). In order to translate the position of the instrument into the 3D model coordinate frame, the instrument location calculator 420 may use data representing the topography of the 3D model, data representing the mapping between the EM field and the coordinate frame of the 3D model, and/or the position of the instrument in the EM field.

In embodiments in which the medical instrument includes an imaging device, an X-ray device, and/or a ultrasound transducer at the distal end of the instrument, the instrument location calculator 420 may be configured to identify one or more anatomical features (e.g., main carina of the trachea) of the patient based on data from the location data repository 415. In some implementations, the instrument location calculator 420 may implement object recognition techniques, by which the instrument location calculator 420 can detect objects present in the field of view of the image data, such as branch openings, lesions, nodules, or particles. Using object recognition, the image analyzer can output object data indicating information about what objects were identified, as well as positions, orientations, and/or sizes of objects represented as probabilities. As one example, object recognition can be used to detect objects that may indicate branch points in a luminal network and then determine their position, size, and/or orientation. In some embodiments, in a given image within a luminal network, each branch will typically appear as a dark, approximately elliptical region, and these regions may be detected automatically by a processor, using region-detection algorithms such as maximally stable extremal regions (MSER) as objects. The instrument location calculator 420 can use light reflective intensity combined with other techniques to identify airways. In some embodiments, the instrument location calculator 420 may be further configured to identify when the distal end of the endoscope has reached the anatomical features, for example via automated feature analysis. In other embodiments, the instrument location calculator 420 may be further configured to determine the location and/or orientation of the distal end of the instrument based on the relative relationship between the distal end of the instrument and the anatomical features. Such image-based analysis can be less susceptible to noise due to patient breathing motion than EM-based analysis. One or more models of the anatomy of the patient as described above may be used with data from the location data repository 415 to identify position and/or orientation of the distal end of the medical instrument.

In some embodiments, the instrument location calculator 420 may use the robotic position data received from surgical robotic system 110 to determine position and/or orientation of the distal end of the medical instrument. For example, the position and/or orientation of the distal end of the medical instrument may be calculated by cumulatively tracking command data instructing the movement of the distal end of the medical instrument (e.g., pitch, roll, yaw, insertion, and retraction of the instrument) or mechanical data representing mechanical movement of the distal end of the instrument (e.g., movement of controllers, pull wires, tendons, or shafts).

In other embodiments, the instrument location calculator 420 may receive data from the location sensor data repository 415 and the respiration frequency and/or phase identifier 430 and use such data to reduce "noise" in the signal received from the location sensors due to cyclic movement of the luminal network of the patient. For example, in some implementations, instrument location calculator 420 can generate a filter based on the determined respiration frequency and apply the filter to the data from the location sensors. In another implementation, instrument location calculator 420 can identify a magnitude of displacement of one or more respiration sensors during respiration and can apply the displacement value as a bias to the position indicated by the location sensor data. This can be performed dynamically, for example by identifying respiration sensor displacement at time $t_n$ and applying that as a bias to the instrument position at time $t_n$, by identifying a next respiration sensor displacement at time $t_{n+1}$ and applying that as a bias to the instrument position at time $t_{n+1}$, and so on. Methods to compensate location data for cyclic respiratory movement of a patient are described in U.S. Provisional Patent Application No. 62/480,257, filed Mar. 31, 2017, titled "Robotic Systems For Navigation of Luminal Networks that Compensate for Physiological Noise," the disclosure of which is hereby incorporated by reference.

In some embodiments, the system 400 may include the respiration frequency and/or phase identifier 430. Respiration frequency and/or phase identifier 430 is a module configured to receive data from the respiration sensor data repository 425 and analyze such data to calculate the frequency and/or phase of respiration. Frequency refers to the time interval between successive phases, for example between successive cycles of inspiration and expiration. Phase refers to whether the respiration cycle is an inspiration phase (e.g., while the patient is inhaling) or an expiration phase (e.g., while the patient is exhaling). Some embodiments can use a Fourier transform to extract the frequency of respiration from the respiration sensor data, using data from one or all of the sensors in various embodiments.

Instrument movement calculator 450 is a module configured to receive data from the sample location calculator 410 and/or the instrument location calculator 420 and/or additionally from the respiration frequency/phase identifier 430 in some embodiments, and analyze such data to determine movement of the medical instrument (e.g., one or more routes of the distal end of the medical instrument) to the one or more sample locations within the biopsy pattern. The movement of the medical instrument may be selected by a user or may be automatically determined by the instrument movement calculator 450. In some embodiments, the user is capable of selecting the location of the target by interfacing with a computer display that can show the biopsy pattern and/or the 3D model, such as by clicking with a mouse or touching a touchscreen. In other embodiments, the movement may be identified programmatically (e.g., by analysis of the model and/or the biopsy pattern) to derive a shortest path to the samples locations within the biopsy pattern. The path may be identified by a physician, or an automatically-identified path may be modified by a physician.

In some embodiments, the instrument movement calculator 450 may be further configured to adjust the movement of the instrument to the one or more positions based on information from the user. For example, the movement of the medical instrument before and/or after each step of the adjustments may be shown to a user via a user input device (e.g., command console 105 or command console 200) and/or may be adjusted by inputs of the user. The movement of the medical instrument may be saved in one or more computer-readable memories (e.g., memories in control and sensor electronics 184) after each adjustment. At the user's command, the instrument movement calculator 450 may transfer the data regarding the movement of the instrument to the instrument controller 460, which will be described below, to guide the distal end of the instrument. In another example, after the medical instrument collects one or more biopsy samples, the instrument movement calculator 450 may be configured to adjust the movement based on an actual movement the instrument takes to collect the biopsy samples and/or actual locations at which the instrument collect the biopsy samples as detected by movement of the medical instrument (e.g., by the location sensors described above). In some embodiments, the data may specify, directly or indirectly, a change in a location, orientation, route, position, etc. for the instrument. For example, the data may comprise one or more routes that the medical instrument takes to reach one or more sample locations within the biopsy patterns. Alternatively or additionally, the data may comprise location, orientation, pitch, roll, yaw, insertion, retraction, and/or deflection angles of the distal end of the medical instrument.

The instrument controller 460 is a module that receives data from the instrument movement calculator 450 and uses this data to direct operation of the surgical robotic system 110 to guide the distal portion of the instrument to one or more sample locations within the biopsy pattern. The instrument controller 460 may be configured to direct mechanical movement of an elongate member of the medical instrument (e.g., motion of one or more pull wires, tendons or shafts of the instrument). In some embodiments, the instrument controller 460 may guide the distal end of the medical instrument to the first sample location within the biopsy pattern, wait until receiving a user input confirming the collection of the first biopsy sample in the first sample location, and then guide the distal end of the medical instrument to the second sample location in response to the confirmation of collecting the first sample. These steps may be repeated for collection of more biopsy samples.

Figure 5A:
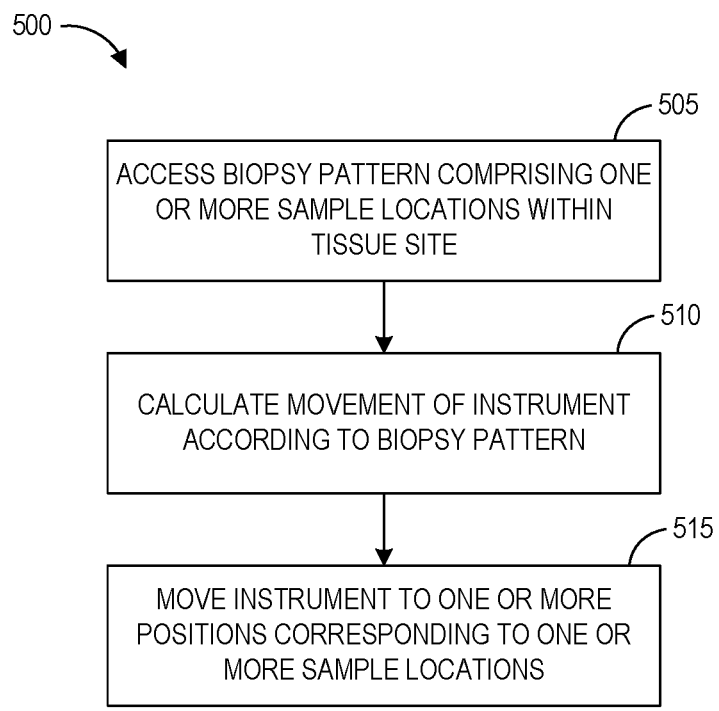
FIG. 5A depicts a flowchart of an example process for moving an instrument to aid in obtaining a set of one or more biopsy samples from a tissue site as described herein.

In accordance with one or more aspects of the present disclosure, FIG. 5A depicts a flowchart of an example process 500 for moving an instrument to aid in obtaining a set of one or more biopsy samples from a tissue site as described herein. The process 500 can be implemented in the biopsy guidance system 400 FIG. 4, the control and sensor electronics 184 of FIG. 1, a robotic medical system, such as the surgical robotic system 110 of FIG. 1, and/or the console base 201 of FIG. 2, or component(s) thereof. Although the blocks of the example process 500 may be performed by one or more components of the example systems as discussed above, for ease of description, the example process 500 will be described as being performed by the system. In example implementations, the system may include an instrument through which the one or more biopsy samples can be collected, an actuator configured to control movements of the instrument, at least one computer-readable memory having stored thereon executable instructions, and one or more processors in communication with the at least one computer-readable memory and configured to execute the instructions. In some cases, some blocks of the example process 500 may be performed by a user of the system or performed by the system based on commands received from a user via a user input device.

At block 505, the system may access a biopsy pattern comprising one or more sample locations within the tissue site. In certain embodiment, the biopsy pattern may be accessed based on user input identifying a pattern for the one or more samples within the target tissue site through a user interface. The system may, based on the received used input, access one or more biopsy patterns, for example, from biopsy pattern data repository 405.

At block 510, the system may calculate movement of the instrument according to the biopsy pattern. In certain embodiments, calculating the movement of the instrument may involve calculating at least one position of the set of location sensors and/or a position of a distal end of the instrument based on a data signal from the set of location sensors. The system may thus calculate the movement of the instrument which can be used to move the instrument from the position of the distal end of the instrument to each of the one or more sample locations. In some embodiments, the calculated movement of the instrument may specify, directly or indirectly, a change in a location, orientation, route, position, etc. for the instrument. For example, the calculated movement may comprise one or more routes that the distal portion of the instrument might take to reach one or more sample locations within the biopsy patterns. Alternatively or additionally, the data may comprise location, orientation, pitch, roll, yaw, insertion, retraction, and/or deflection angles of the distal portion of the instrument.

At block 515, the system may move the instrument to one or more positions corresponding to the one or more sample locations. This may include the system moving the distal portion of the instrument based on the movement of the instrument calculated in block 510. The movement of the instrument to the one or more positions may facilitate the collection of one or more biopsy samples from the tissue site. In some example embodiments, the instrument may include a scope configured to reach the tissue site and a collection device configured to pass through the scope to collect the one or more biopsy samples from the tissue site.

Figure 5B:
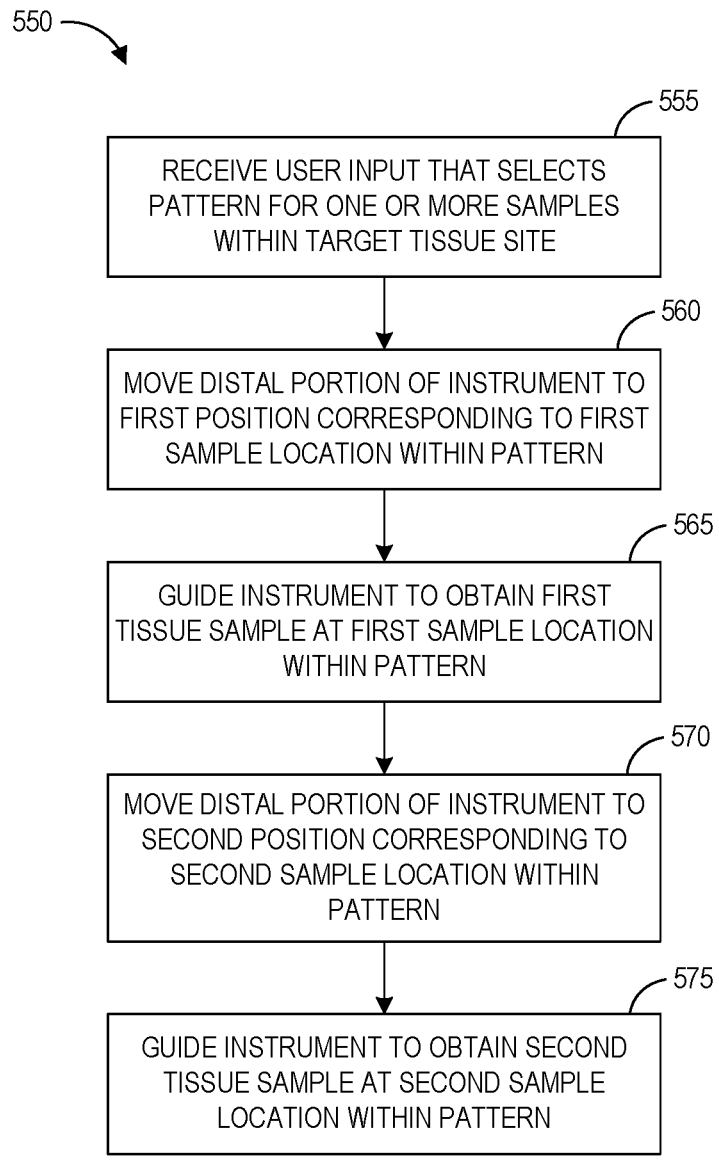
FIG. 5B depicts a flowchart of an example process for guiding an instrument to sample locations for biopsy as described herein.

In accordance with one or more aspects of the present disclosure, FIG. 5B depicts a flowchart of an example process 550 for guiding an instrument for biopsy of one or more samples as described herein. The process 550 can be implemented in the biopsy guidance system 400 FIG. 4, the control and sensor electronics 184 of FIG. 1, a robotic medical system, such as the surgical robotic system 110 of FIG. 1, and/or the console base 201 of FIG. 2, or component(s) thereof. In some cases, some blocks of the example process 550 may be performed by a user of the system, such as block 565.

At block 555, sample location calculator 410 can receive a user input that selects a pattern for the one or more samples within the target tissue site through a user interface. In certain embodiments, the system may, based on the received used input, access one or more biopsy patterns, for example, from biopsy pattern data repository 405. As discussed above, a biopsy pattern may include a set of one or more sample locations at which a biopsy is to be taken place within the target tissue site. In some implementations, the biopsy pattern data may be created or adjusted based on one or more user inputs regarding the biopsy patterns as described above. The biopsy patterns can be any two or three dimensional representation of the sample locations for biopsy within the target tissue site (or a portion of the target tissue site) of the patient. Further, the biopsy patterns can include additional attributes such as penetration depths, one or more sampling velocities, one or more sampling intervals, or one or more sampling forces corresponding to the one or more sample positions.

At block 560, instrument controller 460 may move the distal portion of an instrument to a first position corresponding to a first sample location within the biopsy pattern. This may include the instrument controller 460 receiving data regarding the movement of the instrument (e.g., from the instrument movement calculator 450) and moving the distal portion of the instrument based on the received data. In some embodiments, the data regarding the movement of the instrument may specify, directly or indirectly, a change in a location, orientation, route, position, etc. for the instrument. For example, the data may comprise one or more routes that the distal portion of the instrument might take to reach one or more sample locations within the biopsy patterns. Alternatively or additionally, the data may comprise location, orientation, pitch, roll, yaw, insertion, retraction, and/or deflection angles of the distal portion of the instrument.

As described above, the movement of the instrument toward the first sample location may be calculated (e.g., by the instrument movement calculator 450) based on data from sample location calculator 410, instrument location calculator 420, and/or respiration frequency/phase identifier 430 in some embodiments. Data from sample location calculator 410 is related to sample locations within the biopsy pattern and may be derived from the biopsy pattern data repository 405. Data from instrument location calculator 420 is related to location and/or orientation of the distal portion of the instrument and may be derived from instrument sensor(s) (e.g., EM sensors, imaging devices, X-ray devices, ultrasound transducers, or instrument controllers) and/or location sensor data repository 415. In some embodiments, data from the respiration frequency/phase identifier 430 is related to movement of the anatomical structures of the patient due to respiration and may be derived from respiration sensor(s) and/or respiration sensor data repository 425.

At block 565, the method 550 may involve guiding the instrument to obtain a first tissue sample at the first sample location within the biopsy pattern. In some embodiments, the instrument (e.g., endoscope 115) provides a guide or path for a collection device that can be inserted through or along the instrument to collect the first tissue sample at the first sample location within the biopsy pattern. For example, in some embodiments, the first tissue sample may be manually collected by the user via the collection device, for example, by manually inserting a collection device through the working channel 320 of the endoscope 115. As noted above, at block 560, the instrument controller 460 can position the instrument at the first sample location within a pattern, which, in turn, can aid the user in collecting the first tissue sample at the first sample location by providing a path or guide for the collection device. In another embodiment which will be described below, the instrument may include a robotically controlled collection device, and the instrument controller 460 may control the movement of the collection device and actuate the collection device to collect the first tissue sample at the first sample location.

Block 565 may conclude when the instrument controller determines that the tissue sample has been collected at the first sample location. The instrument controller may determine that the tissue sample has been collected based on, in accordance to some embodiments, the instrument controller receiving a notification that collection of tissue samples (e.g., the first tissue sample) from the user is complete via the user input device (e.g., command console 200). In some cases, the user input device may prompt the user to indicate that the collection step is complete. In some embodiments, the instrument controller may detect the collection of tissue samples (e.g., the first tissue sample) from sample locations (e.g. the first sample location), for example, using location sensors (e.g., imaging devices, ultrasound transducers, X-ray devices, and/or EM sensors).

At block 570, instrument controller 460 move the distal portion of the instrument to a second position corresponding to a second sample location within the biopsy pattern. This may include the instrument controller 460 receiving data regarding the movement of the instrument (e.g., from the instrument movement calculator 450) and moving the distal portion of the instrument based on the received data. As described above, the movement of the instrument toward the second sample location may be calculated (e.g., by the instrument movement calculator 450) based on data from sample location calculator 410, instrument location calculator 420, and/or respiration frequency/phase identifier 430 in some embodiments.

At block 575, the method 550 may involve guiding the instrument to obtain a second tissue sample at the second sample location within the biopsy pattern. As noted above with respect to block 565, in some embodiments, the instrument (e.g., endoscope 115) provides a guide or path for a collection device that can be inserted along or through the instrument to collect a second tissue sample at the second sample location within the biopsy pattern. For example, in some embodiments, the biopsy collection is manually conducted by manually inserting a collection device through the working channel 320 of the endoscope 115. As noted above, at block 570, the instrument controller 460 can position the instrument at the second sample location within the pattern, which can aid the user in collecting the second tissue sample at the second sample location by providing a path through or along the instrument (e.g., through the working channel 320) towards the second sample location. In another embodiment in which the biopsy collection is robotically controlled, the instrument controller 460 may control the movement of a collection device of the instrument and direct the collection device to collect the second tissue sample at the second sample location. One or more of the blocks described above can be repeated for additional sampling locations within the pattern.

Figure 6A:
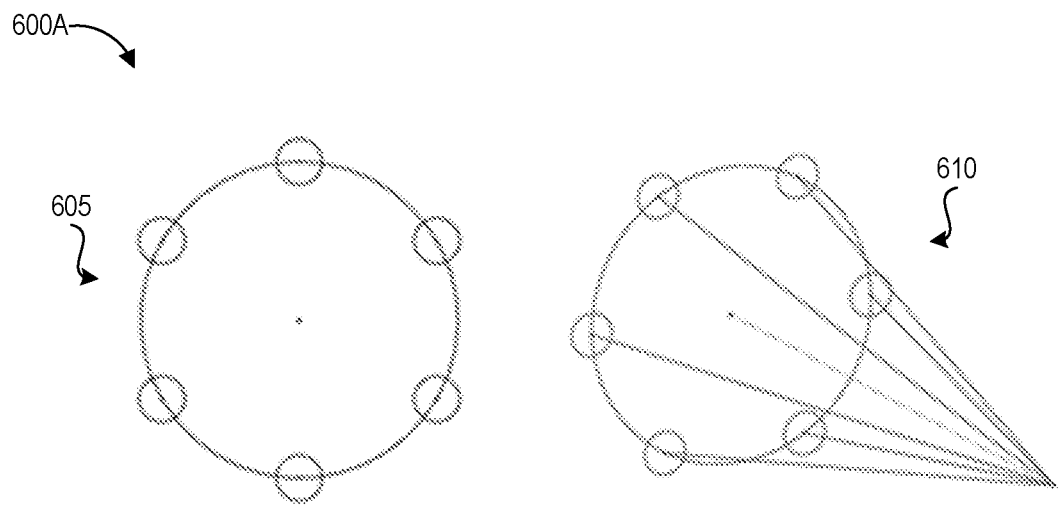
FIGS. 6A and 6B depict example patterns for biopsy as described herein.
Figure 6B:
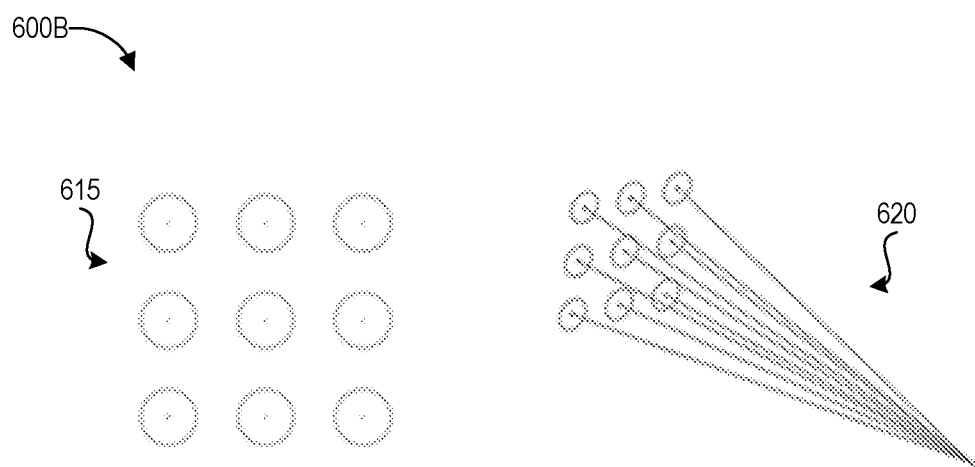

In accordance with one or more aspects of the present disclosure, FIGS. 6A and 6B describe example biopsy patterns and example movements of the distal end of the medical instrument to sample locations within the biopsy patterns.

FIG. 6A depicts one example biopsy pattern data 600A that includes a biopsy pattern 605 comprising a set of sample locations at which biopsy tissues are to be collected and a movement 610 of the distal end of the medical instrument toward the sample locations. The biopsy pattern 605 comprises six sample locations arranged in a two-dimensional circle that is on a plane perpendicular to a longitudinal axis of an elongate member of the medical instrument. The movement 610 of the distal end of the medical instrument shows the shortest linear paths from the distal end of the medical instrument, whose orientation is directed toward the center of the circular biopsy pattern 604, to the six sample locations.

FIG. 6B depicts another example biopsy pattern data 600B that includes a biopsy pattern 615 comprising a set of sample locations and a movement 620 of the distal end of the medical instrument toward the sample locations. The biopsy pattern 615 comprises nine sample locations arranged in a two-dimensional grid on a plane perpendicular to the longitudinal axis of an elongate member of the medical instrument. The movement 620 of the distal end of the medical instrument shows the shortest linear paths from the distal end of the medical instrument, which is directed toward the center of the grid biopsy pattern 604 in a perpendicular manner, to the nine sample locations.

The biopsy patterns 605 and/or 615 may be derived from user inputs or pre-determined in the biopsy pattern data depository 405 as default biopsy patterns. The biopsy patterns 605 and/or 615 and the movements 610 and/or 620 may be displayed to a user via a user input/output device (e.g., command console 105 or command console 200) and/or may be adjusted by inputs of the user. For example, the user may adjust the number of the sample locations or the size of the shape of the biopsy patterns via the user input device. In another example, the biopsy patterns 605 and/or 615 may be adjusted (e.g., by sample location calculator 410) to conform to a shape and/or a 3D landscape of the target tissue site. In some embodiments, the movement 610 and/or 620 can be modified by the user and/or the biopsy guidance system 400. For example, the movement 610 and/or 620 can be displayed to the user and the user can modify the movement 610 and/or 620 to avoid certain anatomical feature. In some embodiments, the movement 610 and/or 620 and/or the sample locations can be displayed visually to the user and in some embodiments overaged onto an image obtained from the instrument 115.

Overview of Another Example Surgical Robotic System

Figure 7A:
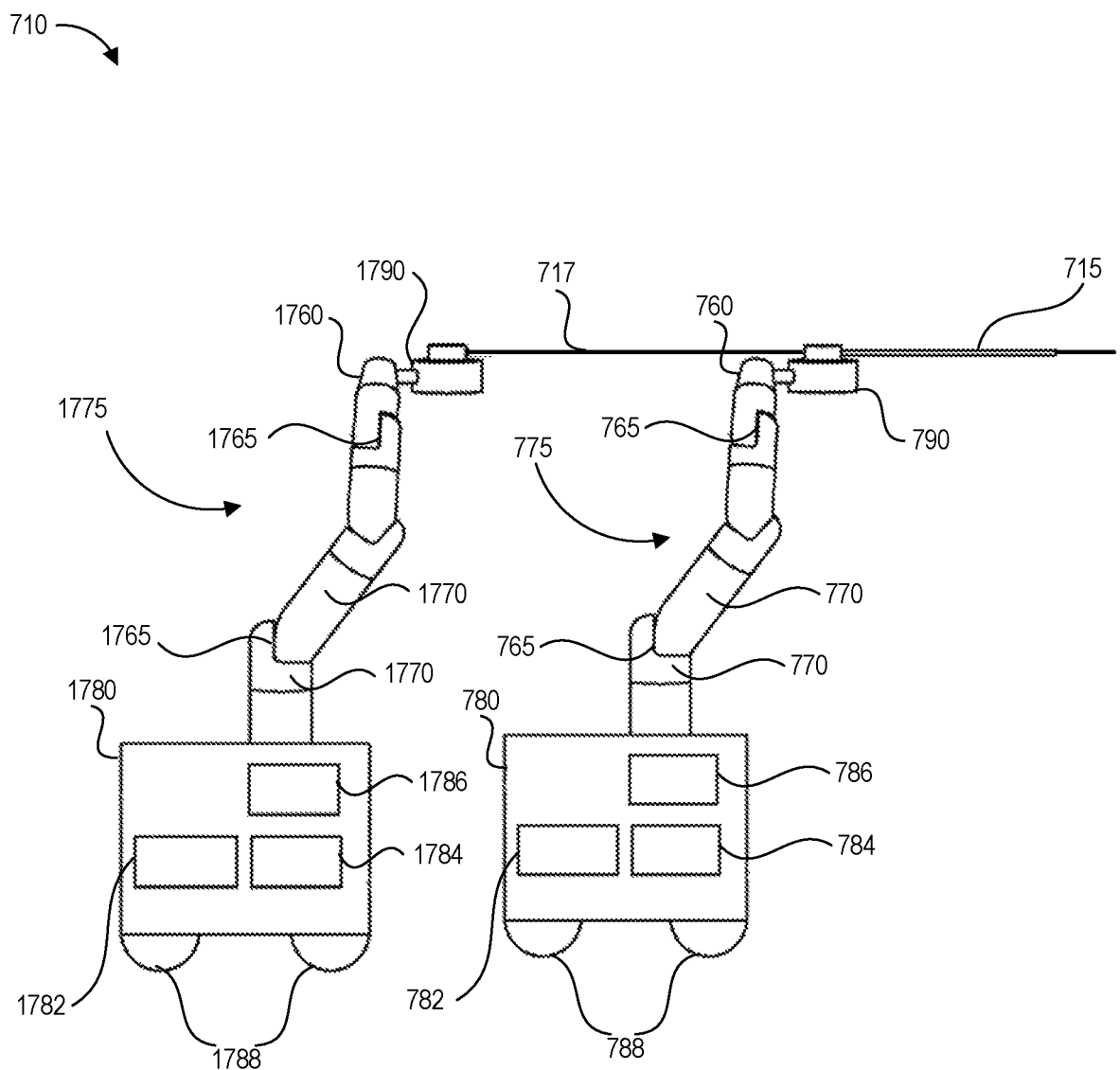
FIGS. 7A and 7B illustrate another example robotic arm for guiding an instrument to sample locations for biopsy.
Figure 7B:
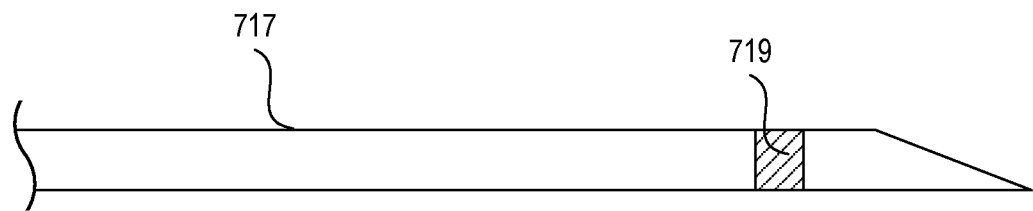

FIGS. 7A and 7B illustrate another example robotic arms 775 and/or 795 of a surgical robotic system 710 as described herein, wherein the surgical robotic system 710 comprises an instrument (e.g., endoscope 715) which comprises a robotically controlled collection device 717 configured to collect biopsy samples. In some cases, the robotically controlled collection device 717 may be controlled by a second robotic arm (e.g., robotic arm 1775), where the collection device is inserted through the working channel of the endoscope 715 controlled by the first robotic arm (e.g., robotic arm 775). Furthermore, it should be appreciated that one or more additional arms may be used in the robotic system 710 to control other components. As one example, an additional arm (e.g., one that is separate from the arms 775 and 1775) may control a sheath. The sheath may be an articulable instrument with a working channel that the endoscope passes through. The purpose of the sheath can be to provide an additional point of articulation to the endoscope and, additionally or alternatively, provide additional structural support to the endoscope.

In FIGS. 7A and 7B, components that can be similar to components described above with reference the embodiment of FIG. 1C and the description above are identified by similar numbers wherein the reference number used is preceded by the numbers "7" and/or "17" instead of "1". For example, components 702, 704 and 706 can be similar to components 102, 104 and 106, respectively, and components 1702, 1704 and 1706 can be similar to components 102, 104 and 106. Reference can be made to the description above for additional descriptions and embodiments of these components which can be used with the embodiment of FIG. 7.

With reference to FIG. 7A, the surgical robotic system 710 includes one or more bases (e.g., base 780 and/or 1780) coupled to one or more robotic arms (e.g., robotic arm 775 and/or 1775). In some embodiments, one or more robotic arms may be coupled to one base. In embodiments similar to one shown in FIG. 7A, each base has a single robotic arm. The robotic arm 775 and/or 1775 includes multiple arm segments 770 and/or 1770 coupled at joints 765 and/or 1765, which provide the robotic arm 775 and/or 1775 multiple degrees of freedom. The robotic arm 775 and/or 1775 may be coupled to an IDM 790 and/or 1790 using a MCI 760 and/or 1760. The IDM 790 and/or 1790 is configured to manipulate medical instruments, for example the endoscope 715 using techniques including direct drive, harmonic drive, geared drives, belts and pulleys, magnetic drives, and the like. The MCI 760 and/or 1760 includes connectors to transfer pneumatic pressure, electrical power, electrical signals, and optical signals from the robotic arm 775 and/or 1775 to the IDM 790 and/or 1790. The robotic arm 775 of the surgical robotic system 710 is configured to manipulate the endoscope 715 using elongate movement members. The elongate movement members may include pull wires, also referred to as pull or push wires, cables, fibers, or flexible shafts.

The base 780 and/or 1780 can include a source of power 782 and/or 1782, pneumatic pressure 786 and/or 1786, wheels 788 and/or 1788, and control and sensor electronics 784 and/or 1784—including components such as a central processing unit, data bus, control circuitry, and memory—and related actuators such as motors to move the robotic arm 775 and/or 1775. The electronics 784 and/or 1784 can implement the biopsy guidance techniques described herein and may also process and transmit control signals communicated from the command console.

The surgical robotic system 710 of FIG. 7A comprises a medical instrument (e.g., endoscope 715) comprising the collection device 717 that is robotically controlled and configured to collect biopsy samples. The collection device 717 is configured to pass through the medical instrument (e.g., through a working channel of the endoscope 715) and to be removably placed within the medical instrument. That way, when the surgical robotic system 710 moves the medical instrument to a target tissue site or sample locations within the biopsy patterns, the collection device 717 inside the medical instrument is also indirectly moved to the sample locations based on the movements of the medical instrument. The surgical robotic system 710 may then actuate the collection device 717 (e.g., via the robotic arm 1775) to obtain biopsy samples from the sample locations. The robotic arm 1775 of the surgical robotic system 710 is configured to manipulate the collection device 717. In this way, some embodiments of the collection device lack the movement capabilities of the medical instrument, thereby decreasing the cost and size of the collection device. However, via the medical instrument, the system provides the movement capabilities for the collection device to move, albeit indirectly, to multiple sample locations for a given nodule.

With reference to FIG. 7B, the collection device 717 may comprise a needle. In some embodiments, the collection device 717 may further comprise a marker 719 at or near a distal end of the collection device 717. The marker 719 may be radiopaque, and examples of radiopaque materials for the marker 719 include, but are not limited to, gold, silver, tungsten, platinum, tantalum, iridium, or their alloys, or radiopaque polymeric compounds.

Figure 8:
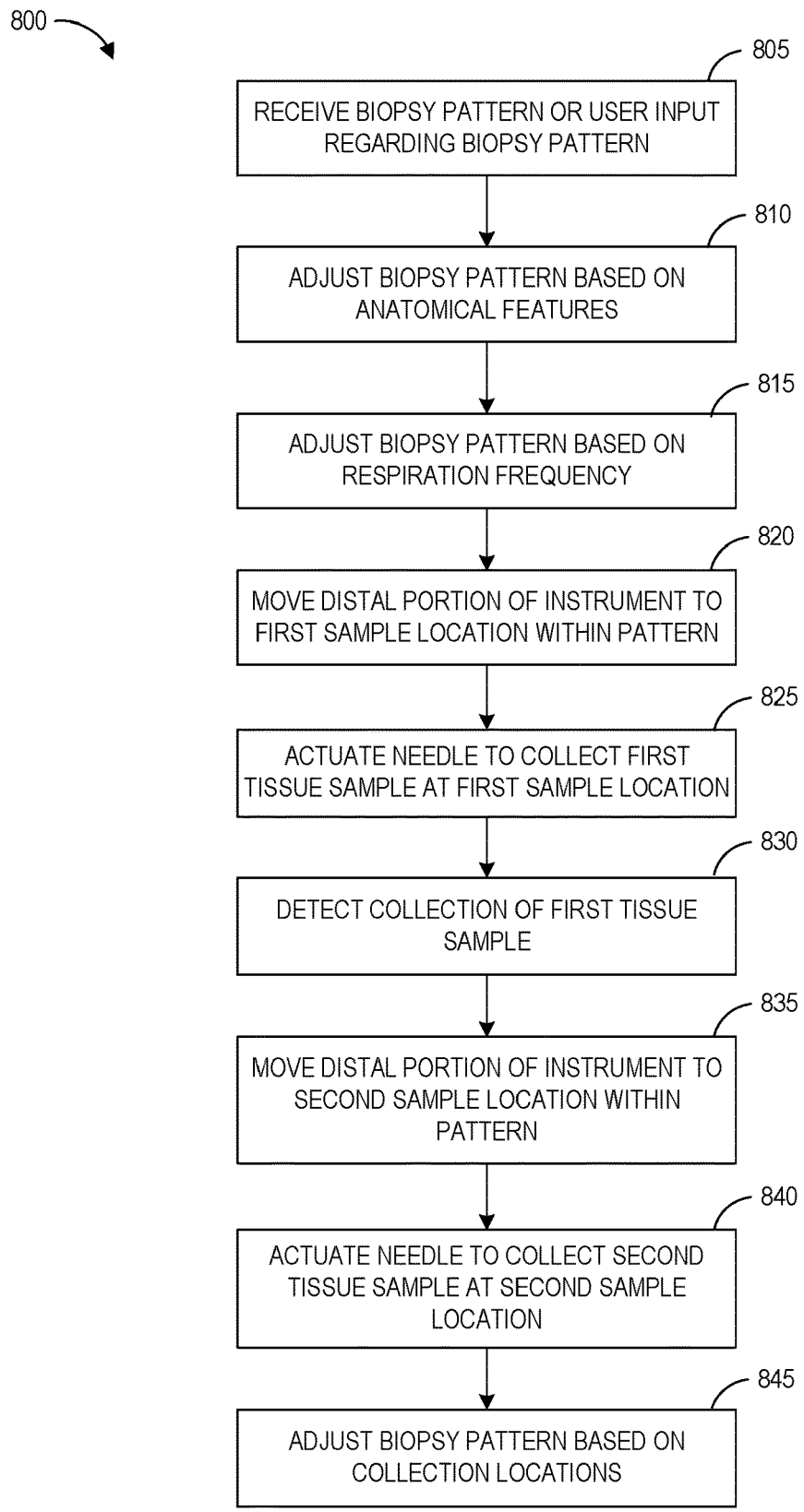
FIG. 8 depicts a flowchart of another example process for guiding an example instrument to sample locations for biopsy as described herein.

In accordance with one or more aspects of the present disclosure, FIG. 8 depicts a flowchart of an example process 800 for guiding a medical instrument (e.g., endoscope 715) for biopsy of one or more samples as described herein. The process 800 can be implemented in a biopsy guidance system, which can be similar to the biopsy guidance system of 400 of FIG. 4, controlling the surgical robotic system 710 of FIG. 7, the control and sensor electronics 784 of FIG. 7, or component(s) thereof.

At block 805, the biopsy guidance system (e.g., a sample location calculator similar to the sample location calculator 410) can access one or more biopsy patterns (e.g., from biopsy pattern data repository similar to the biopsy pattern data repository 405). For example, the biopsy patterns may include one or more sample locations at which biopsy samples are to be collected. In some embodiments, the biopsy patterns can be any two or three dimensional representation of the sample locations for biopsy within the target tissue site (or a portion of the target tissue site) of the patient. In another embodiment, the biopsy patterns may further include one or more penetration depths, one or more sampling velocities, one or more sampling intervals, or one or more sampling forces of the medical instrument at the one or more sample locations. In some implementations, at least portions of the biopsy pattern data (e.g., biopsy pattern shapes) may be pre-determined and saved in the biopsy guidance system (e.g., biopsy pattern data repository). In other implementations, the biopsy pattern data may be determined and/or adjusted based on one or more user inputs regarding the biopsy patterns as described above. For example, the user inputs may determine various aspects of the biopsy patterns including but not limited to the number of sample locations within the biopsy patterns; the size and the location of the biopsy patterns; or penetration depths, sampling velocities, sampling intervals, or sampling forces at the sample locations.

At block 810, the biopsy guidance system (e.g., the sample location calculator) can adjust the biopsy patterns based on anatomical features of the patient during an adjustment stage. In some implementations, the anatomical features of the patient may be determined by data derived from location sensors (e.g., imaging devices, ultrasound transducers, X-ray devices, and/or EM sensors) and/or 3D model data as described above. Various implementations of the adjustment stage that may be conducted in addition to or in replacement of block 810 are described in more detail with respect to FIGS. 9A-9C, which are described below.

At block 815, in some embodiments, the biopsy guidance system (e.g., the sample location calculator) may adjust the biopsy patterns based on the respiration frequency in order to compensate for the cyclic movement of the anatomical structures of the patient due to respiration. A respiration frequency and/or phase identifier (e.g., one similar to the respiration frequency and/or phase identifier 410) can extract the frequency of the respiration from the data from the respiration sensor(s), for example by using a Fourier transform to extract the frequency of the respiration. The Fourier transform can be applied to data from one or more sensors in embodiments having multiple respiration sensors. In one example embodiment, the biopsy patterns may be adjusted by the biopsy guidance system determining the respiration frequency and actuating the collection device at the same or similar points in the respiration cycle. In this way, the biopsy guidance system may take samples at a point in the respiration cycle that is consistent across multiple samples.

At block 820, the biopsy guidance system (e.g., an instrument movement calculator similar to the instrument movement calculator 450) may calculate the movement of the medical instrument (e.g., endoscope 715) toward the sample locations within the biopsy pattern and, based on such data, may move the distal end of the instrument to the first sample location within the biopsy pattern. The latter step may be conducted, for example, by an instrument controller similar to the instrument controller 460. As described above, the movement of the medical instrument toward the first sample location may be calculated (e.g., by the instrument movement calculator) based on data from a sample location calculator (e.g., one similar to the sample location calculator 410), an instrument location calculator (e.g., one similar to the instrument location calculator 420), and/or a respiration frequency/phase identifier (e.g., one similar to the respiration frequency/phase identifier 430) in some embodiments.

At block 825, the biopsy guidance system (e.g., a controller of the collection device 717 or an instrument controller similar to the instrument controller 460) may actuate the collection device 717 (e.g., needle) to collect the first tissue sample from the first sample location within the biopsy patterns. In some embodiments, the biopsy guidance system may distally move the collection device 717 through a working channel of the medical instrument (e.g., one similar to the working channel 320) such that the collection device 717 slides out of the distal end of the medical instrument and inserts into the target tissue site to collect the first tissue sample from the first sample location.

At block 830, in some embodiments, the biopsy guidance system (e.g., the collection device controller or the instrument controller) may detect the collection of the first tissue sample from the first sample location. In some implementations, the biopsy guidance system may receive a notification of collection of the first tissue sample from the user via the user input device (e.g., a command console similar to the command console 200). In another implementation, the biopsy guidance system may track the movement of the collection device 717 using location sensors (e.g., imaging devices, ultrasound transducers, X-ray devices, and/or EM sensors). For example, the biopsy guidance system may track the movement of the collection device (e.g., a needle) via a radiopaque marker (e.g., marker 719) at the distal end of the collection device 717 using an X-ray device (e.g., X-ray image intensifier and X-ray imaging device).

At block 835, the biopsy guidance system (e.g., the instrument controller) may receive data regarding the movement of the medical instrument (e.g., from the instrument movement calculator) and move the distal end of the instrument to the second sample location within the biopsy pattern based on the data. In some embodiments, the data may specify, directly or indirectly, a change in a location, orientation, route, position, etc. for the instrument. For example, the data may comprise one or more routes that the medical instrument takes to reach one or more sample locations within the biopsy patterns. Alternatively or additionally, the data may comprise location, orientation, pitch, roll, yaw, insertion, retraction, and/or deflection angles of the distal end of the medical instrument.

As described above, the movement of the medical instrument toward the second sample location may be calculated (e.g., by the instrument movement calculator) based on data from the sample location calculator, the instrument location calculator, and/or the respiration frequency/phase identifier in some embodiments.

At block 840, the biopsy guidance system (e.g., the collection device controller or the instrument controller) may actuate the collection device 717 to collect the second tissue sample from the second sample location within the biopsy patterns. In some embodiments, the biopsy guidance system may distally move the collection device 717 through a working channel of the medical instrument (e.g., one similar to the working channel 320) such that the collection device 717 slides out of the distal end of the medical instrument and inserts into the target tissue site to collect the second tissue sample from the second sample location.

At block 845, in some embodiments, the biopsy guidance system (e.g., the sample location calculator) may track the movement of the distal end of the collection device 717 to determine actual biopsy locations at which the collection device 717 (e.g., needle) obtained biopsy samples and adjust the one or more sample locations within the biopsy patterns based on the actual biopsy locations. As described above, the movement of the distal end of the collection device 717 may be determined by tracking the radiopaque marker (e.g., marker 719) at the distal end of the collection device 717 using an X-ray device (e.g., X-ray image intensifier and X-ray imaging device).

Although the embodiments of the process 800 described herein are related to a process of collecting biopsy samples at two sample locations, steps similar to blocks 830, 835, and 840 may be conducted for any number of sample locations (e.g., a single location, a third sample location, a fourth sample location, etc.) as well.

Figure 9A:
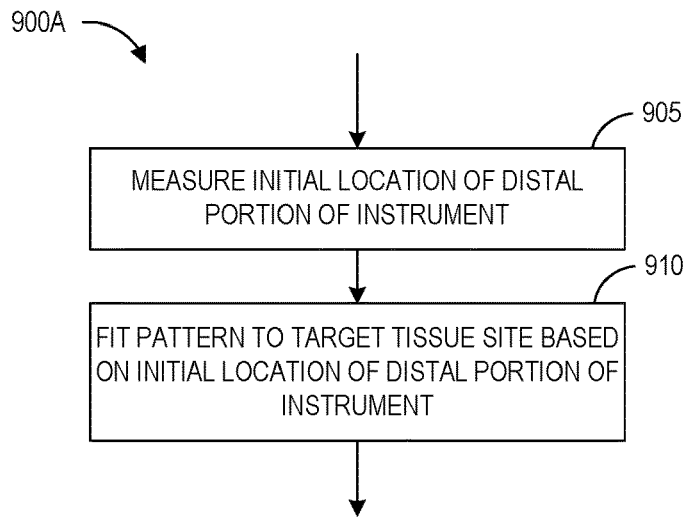
FIGS. 9A-9C depict flowcharts of various example processes that can be used for the adjustment block of FIG. 8.
Figure 9B:
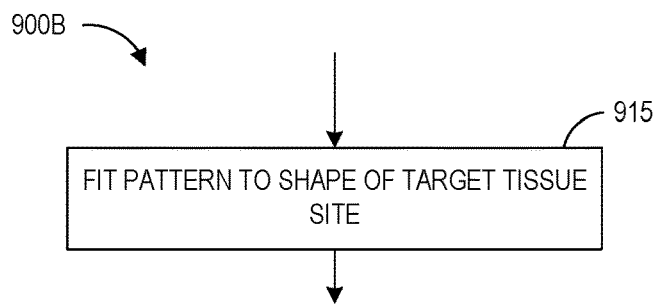
Figure 9C:
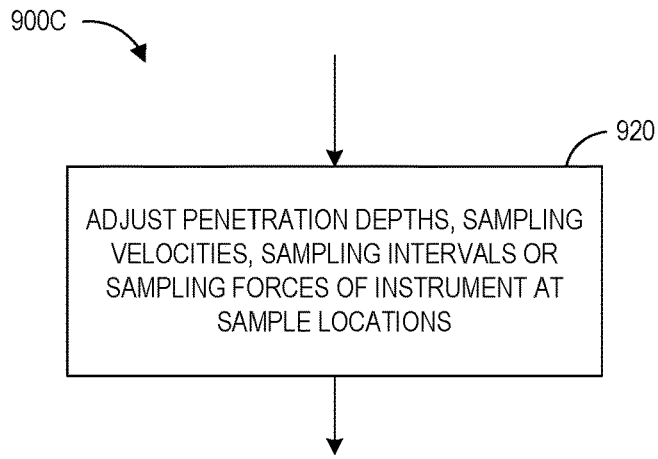

FIGS. 9A-9C depict implementations of the adjustment stage at block 810. With reference to FIG. 9A, depicted is one example process 900A that can be used in addition to or in replacement of block 810 in a manner to adjust the pattern to the target tissue site based on the real-time location of the medical instrument. At block 905, the biopsy guidance system (e.g., instrument location calculator similar to the instrument location calculator 420) determines an initial location of the distal end of the medical instrument (e.g., endoscope 715). The location of the distal end of the medical instrument may be determined by data derived from location sensors (e.g., imaging devices, ultrasound transducers, X-ray devices, and/or EM sensors), robotic position data and/or 3D model data as described above. At block 910, the biopsy guidance system (e.g., sample location calculator similar to the sample location calculator 410) receives data regarding the initial location of the distal end of the medical instrument and fits the biopsy patterns to the target tissue site based on the initial location of the distal end of the medical instrument and the location of the target tissue site. Such fitting may include adjusting the deflection angles such that the when the collection device is actuated, the distal end of the collection device is located within the target tissue site in a manner specified by the biopsy pattern.

With reference to FIG. 9B, depicted is another example process 900B that can be used in addition to or in replacement of block 810 in a manner to adjust the pattern based on data regarding the tissue site, such as shape, location, size, and the like. At block 915, the biopsy guidance system (e.g., sample location calculator similar to the sample location calculator 410) receives data regarding the biopsy patterns and the target tissue site, and fits the biopsy patterns to the shape of the target tissue site. In some embodiments, the data regarding the target tissue site (e.g., shape, location within the preoperative model, or density) may be derived from user inputs (e.g., via a user input device or a command console). In other embodiments, the information about the target tissue site may be based on data derived from location sensors (e.g., imaging devices, ultrasound transducers, and/or X-ray devices) and/or 3D model data. By way of example and not limitation, if the shape of the nodule is spherical, embodiments may receive shape data specifying this spherical shape and, in response, the biopsy guidance system may fit a biopsy pattern that covers the spherical shape. In some cases, the pattern may include a number of samples desired. In this case, the biopsy guidance system may then fit the desired number of samples within the pattern fitted to the spherical shape.

With reference to FIG. 9C, depicted is another example process 900C that can be used in addition to or in replacement of block 810 in a manner to adjust the pattern based on anatomical features of the patient. At block 920, the biopsy guidance system (e.g., sample location calculator similar to the sample location calculator 410) receives data regarding the biopsy patterns and the target tissue site, and adjusts penetration depths, sampling velocities, sampling intervals, or sampling forces of the instrument at sample locations within the biopsy patterns. In some embodiments, the adjustment may be based on anatomical features of the patient (e.g., blood vessels). For example, penetration depths, sampling velocities, or sampling forces of the instrument may be adjusted so that the collection device 717 does not approach areas near the blood vessels.

Some embodiments of the process 800 can use one or more of the processes 900A, 900B, 900C to adjust the biopsy patterns in addition to or in replacement of block 810.

Although the embodiments described herein are to detect and compensate for noise created from a patient's respiration rate, other embodiments may detect and compensate for noise created by other physiological properties of the patient, such as heart rate or any other detectable property. In such cases, where the heart rate may create noise in the EM data, these embodiments may detect the frequency of the heart rate and use the techniques discussed above to remove the noise created by the heart rate. Other noise artifacts may also be detected, as may occur if the patient experiences a periodic tremor or physical movement.

Implementing Systems and Terminology

Implementations disclosed herein provide systems, methods and apparatus for guided biopsy of tissue samples.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components and equivalent mechanisms for producing particular actuation motions. Thus, the present invention is not intended to be limited to the implementations shown herein but is to be accorded the widest scope consistent with the principles and novel features disclosed herein.

What is claimed is:

1. A system configured to aid obtaining a set of a plurality of biopsy samples from a single target location of a luminal network, the system comprising:
   an instrument comprising a distal end through which the plurality of biopsy samples can be collected;
   an actuator configured to control movements of the instrument;
   at least one computer-readable memory having stored thereon executable instructions and a repository configured to store biopsy location patterns; and
   one or more processors in communication with the at least one computer-readable memory and configured to execute the instructions to cause the system to at least:
      drive the instrument through the luminal network to a tissue site providing access to a nodule to be sampled, the instrument configured to access the tissue site via at least one lumen of the luminal network;
      determine, based on user input, a biopsy location pattern comprising at least a first sample location and a second sample location within the tissue site;
      adjust the biopsy location pattern to the tissue site based on a location of the instrument;
      save the adjusted biopsy location pattern to the repository; and
      responsive to one or more user inputs:
         calculate a first movement of the instrument to the first sample location, the first movement comprising a first change in a position of the distal end of the instrument,
         cause the actuator to control movements of the instrument according to the first movement,
         calculate a second movement of the instrument to the second sample location, the second movement comprising a second change in the position of the distal end of the instrument, and
         cause the actuator to control movements of the instrument according to the second movement.

2. The system of claim 1, further comprising a user input device configured to receive the biopsy location pattern, a command to access the biopsy location pattern, or a command to calculate movement of the instrument according to the biopsy location pattern.

3. The system of claim 2, further comprising a user interface screen configured to show the biopsy location pattern.

4. The system of claim 1, wherein the one or more processors are configured to execute the instructions to cause the system to at least: adjust the biopsy location pattern or a route representing the first movement of the instrument to the first sample location and the second movement of the instrument to the second sample location based on information received from a user.

5. The system of claim 1, further comprising:
   a set of one or more location sensors; and
   wherein the one or more processors are configured to execute the instructions to cause the system to at least:
      calculate at least one position of: (1) the set of one or more location sensors or (2) a distal end of the instrument based on a data signal from the set of one or more location sensors; and
      control movement to a plurality of positions based on the calculated at least one position.

6. The system of claim 1, wherein the instrument comprises:
- a scope configured to reach the tissue site; and
- a collection device configured to (1) be removably placed within the scope or (2) pass through the scope and collect the plurality of biopsy samples.

7. The system of claim 6, wherein the one or more processors are further configured to execute the instructions to cause the system to at least: position the scope to a first position, confirm receiving a first sample, and position the scope to a second position in response to a confirmation of receiving the first sample.

8. The system of claim 1, wherein the instrument comprises a collection device configured to obtain the plurality of biopsy samples; wherein the actuator is configured to control movements of the collection device; wherein the collection device further comprises a marker at a distal end of the collection device; and wherein the one or more processors are further configured to execute the instructions to cause the system to at least:
- determine movement of the collection device according to a movement of the marker; and
- adjust at least one of the first sample location and the second sample location according to the movement of the collection device.

9. The system of claim 1, wherein the biopsy location pattern comprises a plurality of sample positions arranged in at least two dimensions.

10. The system of claim 9, wherein the biopsy location pattern comprises a plurality of sample positions arranged in a shape fitted to a shape of the tissue site.

11. The system of claim 9, wherein the biopsy location pattern further comprises at least one of: one or more penetration depths, one or more sampling velocities, one or more sampling intervals, or one or more sampling forces corresponding to the first sample location and the second sample location.

12. An apparatus configured to aid obtaining a plurality of biopsy samples from a single target location of a luminal network, the apparatus comprising:
- at least one computer-readable memory having stored thereon executable instructions and a repository configured to store location patterns for taking samples; and
- one or more processors in communication with the at least one computer-readable memory and configured to execute the instructions to cause the apparatus to at least:
  - drive an instrument of a robotic medical system through the luminal network to a tissue site providing access to a nodule to be sampled, the instrument configured to access the tissue site via at least one lumen of the luminal network, the instrument comprising a distal end through which the plurality of biopsy samples can be collected;
  - determine, based on user input, a location pattern comprising at least a first sample location and a second sample location within the tissue site;
  - adjust the location pattern to the tissue site based on a location of the instrument;
  - save the adjusted location pattern to the repository; and
  - responsive to one or more user inputs:
    - calculate a first movement of the instrument to the first sample location, the first movement comprising a first change in a position of the distal end of the instrument,
    - cause an actuator to control movements of the instrument according to the first movement,
    - calculate a second movement of the instrument to the second sample location, the second movement comprising a second change in the position of the distal end of the instrument, and
    - cause the actuator to control movements of the instrument according to the second movement.

13. The apparatus of claim 12, wherein the one or more processors are configured to execute the instructions to cause the apparatus to at least: calculate (1) at least one position of a set of location sensors or (2) a position of the distal end of the instrument based on a data signal from the set of location sensors; and control movement of the instrument based on the calculated position.

14. The apparatus of claim 12, wherein the one or more processors are configured to execute the instructions to cause the apparatus to at least: calculate movement of a scope according to the location pattern; and guide a distal portion of the scope to the first sample location and the second sample location.

15. The apparatus of claim 12, wherein the one or more processors are configured to execute the instructions to cause the apparatus to at least:
- calculate movement of a collection device according to the location pattern;
- guide a distal portion of the collection device to the first sample location and the second sample location;
- in response to the collection device's collection of the biopsy samples, calculate a plurality of sampling locations at which the collection device obtains the biopsy samples based on the movement of a marker located on the collection device;
- compare the plurality of sampling locations to the first sample location and the second sample location; and
- adjust at least one of the first sample location and the second sample location based on the comparison.

16. The apparatus of claim 12, wherein the location pattern comprises a plurality of sample positions arranged in a shape fitted to a shape of the tissue site.

17. A method for collecting a plurality of samples from a single target location of a luminal network of a patient, the method comprising:
- driving an instrument of a robotic medical system through the luminal network to a target tissue site providing access to a nodule to be sampled, the instrument configured to access the target tissue site via at least one lumen of the luminal network, the instrument comprising a distal end through which the plurality of samples can be collected;
- through a user interface of the robotic medical system, receiving a user input;
- determining, based on the user input, a location pattern comprising at least a first sample location and a second sample location within the target tissue site;
- adjusting the location pattern to the target tissue site based on a location of the instrument;
- saving the adjusted location pattern to a repository of the robotic medical system; and
- responsive to one or more user inputs:
  - calculating a first movement of the instrument to the first sample location, the first movement comprising a first change in a position of the distal end of the instrument,
  - causing an actuator to control movements of the instrument according to the first movement, calculating a second movement of the instrument to the second sample location, the second movement comprising a second change in the position of the distal end of the instrument, and causing the actuator to control movements of the instrument according to the second movement.

18. The method of claim 17, further comprising adjusting the location pattern to the first sample location or the second sample location after receiving the user input.

19. The method of claim 18, wherein adjusting the location pattern is based on one or more anatomical features.

20. The method of claim 18, wherein adjusting the location pattern comprises measuring an initial location of the distal end of the instrument and fitting the location pattern to the tissue site based on the initial location of the distal end of the instrument.

21. The method of claim 20, wherein fitting the location pattern comprises adjusting one or more penetration depths, one or more sampling velocities, one or more sampling intervals, or one or more sampling forces of the instrument at the first sample location or the second sample location.

22. The method of claim 17, further comprising adjusting movement of the distal end of the instrument based on a respiration frequency of the patient when guiding the instrument to obtain a first tissue sample or a second tissue sample.

23. The method of claim 17, wherein causing the actuator to control movements of the instrument according to the second movement occurs after receiving a notification of collection of a first tissue sample based on the first movement of the instrument to the according to the first movement.

24. The method of claim 17, wherein causing the actuator to control movements of the instrument according to the first movement or the second movement comprises: calculating at least one position of the distal end of the instrument based on a data signal from a set of location sensors; and controlling movement of the instrument based on the calculated at least one position.

25. A non-transitory computer readable storage medium having stored thereon instructions that, when executed, cause at least one computing device to at least:

drive an instrument through a luminal network to a target tissue site providing access to a nodule to be sampled, the instrument configured to access the target tissue site via at least one lumen of the luminal network, the instrument comprising a distal end through which a plurality of biopsy samples can be collected;

determine, based on user input, a location pattern comprising at least a first sample location and a second sample location within the tissue site;

adjust the location pattern to the target tissue site based on a location of the instrument;

save the adjusted location pattern to a repository of the at least one computing device; and responsive to one or more user inputs:

calculate a first movement of the instrument to the first sample location, the first movement comprising a first change in a position of the distal end of the instrument, cause an actuator to control movements of the instrument according to the first movement, calculate a second movement of the instrument to the second sample location, the second movement comprising a second change in the position of the distal end of the instrument, and cause the actuator to control movements of the instrument according to the second movement.

26. The non-transitory computer readable storage medium of claim 25, wherein the instructions, when executed, cause the at least one computing device to at least: calculate at least one position of the distal end of the instrument based on a data signal from a set of location sensors; and controlling movement of the instrument based on the calculated at least one position.

27. The non-transitory computer readable storage medium of claim 25, wherein the instructions, when executed, cause the at least one computing device to at least: adjust the location pattern based on one or more anatomical features of the tissue site or a respiratory rate of a patient.

28. The non-transitory computer readable storage medium of claim 27, wherein the instructions, when executed, cause the at least one computing device to at least: adjust the location pattern based on one or more blood vessels within the tissue site.

29. A system configured to aid obtaining a set of a plurality of biopsy samples of a nodule from a single target location of a luminal network, the system comprising:

an instrument through which the plurality of biopsy samples of the nodule can be collected;

an actuator configured to control movements of the instrument;

at least one computer-readable memory having stored thereon executable instructions and a repository configured to store biopsy location patterns; and one or more processors in communication with the at least one computer-readable memory and configured to execute the instructions to cause the system to at least:

drive the instrument through the luminal network to a tissue site, the instrument configured to access the tissue site via at least one lumen of the luminal network;

access a biopsy location pattern comprising a plurality of sample locations within the tissue site, the tissue site comprising the single target location of the luminal network within which the plurality of sample locations of a nodule are located;

adjust the biopsy location pattern to the tissue site based on a location of the instrument;

save the adjusted biopsy location pattern to the repository;

calculate a first movement of the instrument to an actual biopsy location at which a first biopsy sample is to be obtained from the tissue site;

track a location of the instrument after the first movement;

determine, based on the tracked location, the actual biopsy location at which the first biopsy sample is obtained from the tissue site;

update the biopsy location pattern based on the actual biopsy location; and calculate a second movement of the instrument based on the updated biopsy location pattern.

30. The system of claim 29, wherein the at least one computer-readable memory has stored thereon the biopsy location pattern prior to the driving of the instrument through the luminal network to the tissue site.

31. The system of claim 1, wherein a robotic arm comprises the actuator.

* * * * *